United States Patent
Sokoloff et al.

(10) Patent No.: US 8,546,402 B2
(45) Date of Patent: Oct. 1, 2013

(54) CHROMONE DERIVATIVES, A PROCESS FOR THEIR PREPARATION AND THEIR THERAPEUTIC APPLICATIONS

(76) Inventors: Pierre Sokoloff, Belleserre (FR); Thierry Imbert, Viviers les Montagnes (FR); Ludovic Leriche, Castres (FR); Jean-François Patoiseau, Castres (FR); Jean-Pierre Rieu, Castres (FR)

( * ) Notice: Subject to any disclaimer, the term of this patent is extended or adjusted under 35 U.S.C. 154(b) by 0 days.

(21) Appl. No.: 13/393,542

(22) PCT Filed: Aug. 31, 2010

(86) PCT No.: PCT/IB2010/053895
§ 371 (c)(1),
(2), (4) Date: Feb. 29, 2012

(87) PCT Pub. No.: WO2011/027289
PCT Pub. Date: Mar. 10, 2011

(65) Prior Publication Data
US 2012/0157463 A1    Jun. 21, 2012

Related U.S. Application Data

(60) Provisional application No. 61/336,992, filed on Jan. 29, 2010.

(30) Foreign Application Priority Data

Sep. 1, 2009  (FR) ...................... 09 55944

(51) Int. Cl.
A61K 31/496   (2006.01)
C07D 405/06   (2006.01)

(52) U.S. Cl.
USPC ..................... 514/254.11; 544/376

(58) Field of Classification Search
USPC ..................... 544/376; 514/254.11
See application file for complete search history.

(56) References Cited

U.S. PATENT DOCUMENTS

| 5,089,497 A | 2/1992 | Jaen et al. |
| 2005/0197343 A1 | 9/2005 | Gmeiner et al. |

FOREIGN PATENT DOCUMENTS

| EP | 1683790 | 7/2006 |
| WO | 2008009741 | 1/2008 |

OTHER PUBLICATIONS

Sokoloff et al, 2006, CNS & Neurological Disorders—Drug Targets, vol. 5, p. 25-43.*
Beaulieu et al, Pharmacological Reviews, 2011, vol. 63, p. 182-217.*
Nicola et al, 2007, Biochemical and Biophysical Research Communications, vol. 358, No. 3, p. 686-691, Supplementary Data.*
Hackling, Anneke et al. "N-(.omega.-4-(2-Methoxyphenyl)piperazin-l-yl)alkyl)carboxamides as Dopamine D2 and D3 Receptor Ligands", Journal of Medicinal Chemistry, vol. 46, No. 18, Jan. 1, 2003, pp. 3883-3899, American Chemical Society, Washington, U.S.
Butini, S. et al. "Discovery of a new class of potential multifunctional atypical antipsychotic agents targeting dopamine d3 and serotonin 5-HT 1A and 5-HT2A receptors: Design, synthesis, and effects on behavior", Journal of Medicinal Chemistry, vol. 52, No. 1, Jan. 8, 2009, pp. 151-169, American Chemical Society, U.S.A.
Micheli, F. et al. "Selective dopamine D3 receptor antagonists. A decade of progress: 1997-2007", Expert Opinion on Therapeutic Patients, vol. 18, No. 8, Aug. 2008, pp. 1354-3776.
International Search Report for related PCT Application No. PCT/IB2010/053895 dated Nov. 4, 2010 (3 pp.).
French Search Report for related French Application No. 0955944 dated Jan. 10, 2010 (2 pp.).

* cited by examiner

*Primary Examiner* — Wu-Cheng Winston Shen
*Assistant Examiner* — Karen Cheng
(74) *Attorney, Agent, or Firm* — Winthrop & Weinstine, P.A.

(57) ABSTRACT

The present invention relates to chromone derivatives, their preparation, their pharmaceutical compositions and their application as D3 dopaminergic ligands as a medicament for disorders of the central nervous system.

15 Claims, No Drawings

CHROMONE DERIVATIVES, A PROCESS FOR THEIR PREPARATION AND THEIR THERAPEUTIC APPLICATIONS

CROSS-REFERENCE TO RELATED APPLICATIONS

This application is the §371 National Stage Application of PCT Patent Application No. PCT/IB2010/053895, filed Aug. 31, 2010, which claims priority to French Patent Application No. 0955944, filed Sep. 1, 2009, and U.S. Provisional Application No. 61/336,992, filed Jan. 29, 2010. The entire contents of the aforementioned patent applications are incorporated herein by this reference.

The invention relates to chromone derivatives, to processes for their preparation, to pharmaceutical compositions containing them and to their therapeutic applications as agonists, partial agonists or antagonists of the dopamine receptor D3 (DRD3) for the treatment of various neurological and psychiatric conditions.

Schizophrenia is a term used to describe a group of pathologies of unknown origin that affects approximately 1% of the general population. This pathology is characterised by a variety of symptoms, classified as positive symptoms (hallucinations, deliria, disorganised thought) and negative symptoms (social withdrawal and affective flattening), at an age commencing in adolescence or the beginning of adulthood, and can persist in chronic form with episodes of exacerbation for many years.

Patients affected by schizophrenia can be treated with medicaments called neuroleptics, also known by the name antipsychotics. The therapeutic effect of antipsychotics is generally acknowledged as resulting from the blockade of receptors of the neuromediator dopamine in the brain. There are five known sub-types of dopamine receptors, called D1, D2, D3, D4 and D5 (Sokoloff, P. et al., Novel dopamine receptor subtypes as targets for antipsychotic drugs. *Annals New-York Academy of Sciences* 1995, 757, 278) and the conventional antipsychotics are D2 and D3 receptor antagonists. However, antipsychotics are frequently responsible for undesirable extrapyramidal side-effects (EPS) and abnormal movements called tardive dyskinesias, which are attributed to the blockade of D2 receptors in the striatal region of the brain. Blockade of the D3 receptor (DRD3) has been suggested as being responsible for the therapeutic effects of antipsychotics (Schwartz J. C. et al., *Eur. Neuropsychopharmacol.* 2003, 13(suppl. 4): S166). Hence, pharmacological agents that selectively modulate DRD3 function are considered to be effective antipsychotics free from neurological side-effects (International patent application WO 91/15513).

The selective modulation of DRD3 receptors can be achieved with molecules that bind selectively to DRD3 and that act as agonists, as antagonists or as partial agonists. The antipsychotic activity resulting from the modulation of DRD3 function can be predicted in animals by employing schizophrenic mouse models (Leriche L. et al., *Neuropharmacology* 2003, 45, 174). It has moreover been demonstrated that selective blockade of DRD3, but not the concomitant blockade of DRD2 and DRD3, increases the extracellular levels of dopamine and acetylcholine, another neuromediator, in the prefrontal cortex (Lacroix L. P. et al., *Neuropsychophamacol.* 2003, 28, 839). Dopamine and acetylcholine in that region of the brain are essential for cognitive function. It is consequently thought that selective antagonists of DRD3 can improve cognition, which is altered in schizophrenia and also in neurodegenerative pathologies such as Alzheimer's disease.

Antipsychotics in general, and aripiprazole, quetiapine and olanzapine in particular, are used in the treatment of the acute manic phase of bipolar disorder. Antagonists or partial agonists of DRD3 are thus also considered as medicaments for the treatment of bipolar disorder.

Genetically modified mice carrying a mutation that disables DRD3 (DRD3 "knockout") are less anxious in behavioural tests predictive of an anxiogenic or anxiolytic activity (Steiner H. et al., 1: *Physiol Behav.* 1997, 63, 137-41). Consequently, a pharmacological disablement of DRD3, such as is obtained by using a DRD3 antagonist described in the present invention, is also a treatment for anxiety.

Depression is a common mood pathology that is characterised by feelings of intense sadness, pessimistic thoughts and self-depreciation, often accompanied by loss of energy, enthusiasm and libido. The incapacity to feel pleasure from normally pleasant experiences, also known by the name of anhedonia, is also regarded as a common symptom in depression. A significant role in pleasure and motivation has been attributed to the dopaminergic neurons in a region of the brain called the nucleus accumbens (Koob G. F. et al., *Sem. Neurosci.* 1992, 4, 139; Salamone J. D. et al., *Behav. Brain Res.* 1994, 61, 117). These neurons have consequently been suggested as being implicated in the neurobiology of depression, especially anhedonia, and in the therapeutic effects of some antidepressant medicaments (Kapur S, and Mann J. *Biol. Psychiatry* 1992, 32, 1-17; Willner P., *Int. Clin. Psychopharmacol.* 1997, 12, S7-S14). It has been demonstrated that various antidepressant treatments selectively increase the expression of DRD3 in the nucleus accumbens (Lammers C. H. et al., *Mol. Psychiatry.* 2000, 5, 378), suggesting that increasing DRD3 function could be a new mode of antidepressant treatment. An increase in the function of the D3 receptor DRD3 can be achieved using agonists or partial agonists of DRD3, which might therefore be an effective treatment for depression.

Dependence on drugs or addictive substances, also known as drug addiction, is a chronic and recurrent pathology in which behaviour involving risk-taking and the search for addictive substances, and the compulsive behaviour of drug-taking, persist despite the negative consequences perceived by the patient (Deroche-Gamonet V. et al., *Science* 2004, 305, 1014; Vanderschuren L. J. et al., *Science* 2004, 305, 1017). The withdrawal phenomenon that occurs during abstinence from addictive substances can be triggered or exacerbated by environmental stimuli that have acquired a motivational force as a result of having repeatedly been associated with the effects of a drug, both in man (Childress A. R. et al., *Am. J. Psychiatry* 1999, 156, 11; Robinson T. E. et al., *Brain Research Reviews* 1993, 18, 247) and in animals (Goldberg S. R. et al., *NIDA Res. Monogr.* 1981, 37, 241; Arroyo M. *Psychopharmacology* 1999, 140, 331). In animals, highly selective DRD3 agonists or partial antagonists specifically reduce the responses to stimuli associated with cocaine (Pilla M. *Nature,* 1999, 400, 371; Le Foll, B. *Eur. J. Neurosci.* 2002, 15, 2016; Vorel S. R. *J. Neurosci.* 2002, 22, 9595), with an opiate (Frances H. et al., *Neuroreport* 2004, 15, 2245) or with nicotine (Le Foll B. et al., *Mol. Psychiatry.* 2003, 8, 225), while having no influence on the primary effects of the drugs. The density of DRD3 is abnormally high in the brain of cocaine addicts (Staley J. K. et al., *J. Neurosci.* 1996, 16, 6106). Partial agonists or antagonists of DRD3 are therefore thought to be effective medicaments for facilitating abstinence and reducing the risk of relapse.

Parkinson's disease is a pathology characterised by tremor at rest, limb rigidity and akinesia (difficulty in initiating movements). The disease is caused by a degeneration of dopaminergic neurons. The treatment of Parkinson's disease is based on the substitution of dopamine through the administration of L-dihydroxyphenylamine (L-DOPA) or direct dopamine agonists. Long-term use of L-DOPA, however, is associated in a very significant number of cases with the occurrence of abnormal movements called dyskinesias. It has been demonstrated in a non-human primate model of Parkinson's disease that the modulation of DRD3 with a highly selective partial agonist attenuates dyskinesias (Bezard E. et al., *Nat. Med.* 2003, 6, 762). The compounds described in the present document are consequently considered as additive treatments in Parkinson's disease. It has, moreover, been demonstrated that a DRD3 agonist increases neurogenesis in the rat, so that DRD3 agonists might also be medicaments that delay progression of the disease.

A mutation in the DRD3 gene is associated and co-segregated with essential tremor, a common and hereditary neurological disorder that is characterised by action tremor of all or part of the body in the absence of any other neurological pathology (Jeanneteau et al., *Proc. Natl. Acad. Sci. USA* 2006, 103, 10753). The mutation increases DRD3 function. The normalisation of DRD3 function by using partial agonists or antagonists of DRD3 might therefore be an effective treatment for essential tremor.

Dopamine controls erectile function and dopaminergic agents have been proposed as a treatment for erectile dysfunction (Guiliano F., Ramplin O. *Physiol Behav.* 2004, 83, 189-201). More specifically, the pro-erectile effects of dopaminergic agonists are mediated by the D3 receptor in rodents (Collins G. T. et al., *J. Pharmacol. Exp. Ther.,* 2009, 329, 210-217) and a selective D3 receptor antagonist delays ejaculation during coitus in the rat (Clement P. et al., *J. Sex. Med.,* 2009, 6, 980-988). Agonists, partial agonists and antagonists of DRD3 such as those described in the present invention may thus be a treatment for various dysfunctions of erectile function.

The literature mentions phenylpiperazine chromones for use in combating malaria in *Biochemical and Biophysical Research Communications* 2007, 358(3), 686. *Indian J. Chem., section B*, 2002, 41B(4), 817, describes phenylpiperazinomethylchromone compounds. Mannich bases using methoxychromones are known from *Farmaco Edizione Scientifica* 1977, 32, (9), 635. A patent specification, U.S. Pat. No. 3,410,851, describes flavones having anticonvulsive, analgesic or bronchodilatory properties. The compounds of the present invention are distinguished by the fact that they have a carbon chain of 4 methylenes between the chromone moiety and phenylpiperazine, which confers upon them the property of being dopaminergic D3 receptor ligands.

The patent applications WO2003028728, WO2004004729 and WO2006077487 and the patent specification EP1841752 describe heteroaryl phenylpiperazine butyl carboxamides as DRD3 ligands. Patent application WO2008009741 mentions chromene and thiochromene carboxamides demonstrating an affinity for the D3 dopaminergic receptor for use as antipsychotics. Patent application WO2006072608 mentions arylpiperazines having dopaminergic and serotonergic receptor modulating properties for use in neuropsychiatric disorders such as schizophrenia. The publication *J. Med. Chem.* 2009, 52, 151 also mentions those same derivatives. All of the products described in the above-cited patent specifications have a carboxamide chain in their structure. The products of the present invention are distinguished from the described compounds by the fact that they do not have a carboxamide chain but, unexpectedly, are potent D3 dopaminergic receptor ligands.

As used above, the term "D3 dopamine receptor", "D3 receptor" or "DRD3" denotes a dopamine receptor sub-type chiefly expressed in the limbic system (Sokoloff P et al., *Nature,* 1990, 347, 146-151). DRD3 is described in international patent application WO 91/15513.

As used above, the term "D3 receptor partial agonist" denotes a compound that forms a complex with DRD3 and acts as a combined agonist-antagonist, that is to say it induces a physiological response of an intensity lower than that of the natural mediator, dopamine. In vitro, in a cell expressing DRD3, a DRD3 partial agonist produces an active response the maximum intensity of which is lower than that produced by dopamine or by a full agonist, for example quinpirole (trans(−)-4aR-4,4a,5,6,7,8,8a,9-octahydro-5-propyl-1H(or 2H)pyrazolo[3,4g]quinoline). A DRD3 partial agonist may also partially prevent the response produced by dopamine or its full agonists. In vivo, a DRD3 partial agonist produces dopaminergic responses, especially when the levels of dopamine are reduced, as is the case in rats having lesions caused by 6-hydroxydopamine or in monkeys intoxicated with 1 methyl-4-phenyl-1,2,3,6-tetrahydropyridine (MPTP). In addition, in vivo a DRD3 partial agonist may act as an antagonist, especially when the DRD3 is subject to sustained stimulation by dopamine.

"A DRD3 antagonist" denotes a molecule that forms a complex with DRD3 and is capable of preventing a response triggered by dopamine or an agonist thereof in a cell expressing DRD3.

As used here, the term "salts" denotes inorganic acid and base addition salts of the compounds of the present invention. Preferably, the salts are pharmaceutically acceptable, that is to say, they are non-toxic for the patient to whom they are administered.

The expression "pharmaceutically acceptable" refers to molecular entities and compositions that do not produce any adverse allergic effect or other undesirable reaction when administered to an animal or human.

When used herein, the expression "pharmaceutically acceptable excipient" includes any diluent, adjuvant or excipient, such as preservative, filler disintegrator, wetting agent, emulsifier, dispersant, antibacterial or antifungal agent, or also agents that would allow intestinal and digestive absorption and resorption to be delayed. The use of those media or vectors is well known in the art. Except where the agent is chemically incompatible with a chromone derivative, its use in pharmaceutical compositions containing the compounds according to the invention is envisaged.

In the context of the invention, the term "treatment" as used herein means preventing or inhibiting the appearance or progression of the condition to which the term is applied, or of one or more symptoms of that condition.

"Therapeutically active amount" means an amount of a chromone derivative that is effective in obtaining the desired therapeutic effect according to the invention.

According to the invention, the term "patient" refers to a human or non-human mammal affected or very susceptible to being affected by a pathology. Preferably, the patient is a human.

In the context of the present invention, a C1-4alkyl group is understood as a linear or branched hydrocarbon chain containing from 1 to 4 carbon atoms, for example a methyl group, an ethyl group, a propyl group or a butyl group.

In the context of the present invention, a $C_{1-4}$alkoxy group is understood as a linear or branched hydrocarbon chain containing from 1 to 4 carbon atoms and an oxygen atom, for example a methoxy group, an ethoxy group, a propoxy group or a butoxy group.

In the context of the present invention, a $C_{1-4}$thioalkoxy group is understood as a linear or branched hydrocarbon chain containing from 1 to 4 carbon atoms, an oxygen atom and a sulfur atom, for example a thiomethoxy group, a thioethoxy group, a thiopropoxy group or a thiobutoxy group.

In the context of the present invention, a $C_{1-4}$dialkylamino group is understood as an amine disubstituted by linear or branched $C_{1-4}$alkyl groups, for example a dimethylamino group, a diethylamino group, a dipropylamino group or a dibutylamino group.

In the context of the present invention, halogen is understood as fluorine, chlorine or bromine.

In the context of the present invention, a $C_{1-4}$haloalkyl group is understood as a $C_{1-4}$alkyl group monosubstituted, disubstituted or trisubstituted by a halogen, for example a $CF_3$ group, a $CHF_2$ group, a $CH_2F$ group, a $CCl_3$ group, a $CHCl_2$ group, a $CH_2Cl$ group, a $CBr_3$ group, a $CHBr_2$ group or a $CH_2Br$ group.

In the context of the present invention, a $C_{1-4}$dialkylaminoalkyl group is understood as a $C_{1-4}$dialkylamino group as defined hereinbefore bonded to a $C_{1-4}$alkyl group by a carbon atom, for example a dimethylaminomethyl group, a dimethylaminoethyl group, a diethylaminomethyl group or a diethylaminoethyl group.

In the context of the present invention, a $C_{1-4}$alkoxyalkyl group is understood as a $C_{1-4}$alkyl group as defined hereinbefore bonded to a $C_{1-4}$alkoxy group by a carbon atom, for example a methoxymethyl group, an ethoxymethyl group, a methoxyethyl group or an ethoxyethyl group.

In the context of the present invention, a $C_{1-4}$hydroxyalkyl group is understood as an alkyl group as defined hereinbefore in which a hydrogen atom is substituted by a hydroxyl group, for example a $CH_2OH$ group, a $C_2H_4OH$ group, a $C_3H_6OH$ group or a $C_4H_8OH$ group.

In the context of the present invention, a $C_{1-4}$alkylcarbonyl group is understood as an alkyl group as defined hereinbefore bonded to a carbonyl group by the carbon atom, for example a $COCH_3$ group, a $COC_2H_6$ group, a $COC_3H_7$ group or a $COC_4H_9$ group.

In the context of the present invention, a $C_{1-4}$alkoxycarbonyl group is understood as an alkoxy group as defined hereinbefore bonded to a carbonyl group by the carbon atom, for example a $COOCH_3$ group, a $COOC_2H_5$ group, a $COOC_3H_7$ group or a $COOC_4H_9$ group.

In the context of the present invention, a $C_{1-4}$-phenylalkyl group is understood as a phenyl group bonded by a carbon atom to an alkyl group as defined hereinbefore.

The invention relates to chromone derivatives, to processes for their preparation, and to their use as a medicament, as DRD3 receptor ligands, for the treatment of neurological or psychiatric diseases, conditions or disorders. Those compounds correspond to the general formula 1.

general formula 1

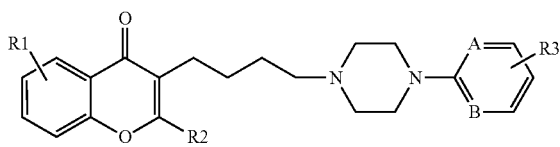

wherein:
R1 represents one or more identical or different substituent(s) on the benzene ring, each representing, independently, a hydrogen atom or a halogen atom, or a $C_{1-4}$alkoxy group or an OH group or a $C_{1-4}$alkyl group or an —$O(CH_2)_nO$— group in which n=1 or 2.

R2 represents a hydrogen atom or a $C_{1-4}$alkyl group.

A and B represent, independently, either a nitrogen atom or a carbon atom.

R3 represents a hydrogen atom or one or more identical or different substituent(s) selected from the group composed of: a halogen atom, a $C_{1-4}$alkyl group, a $C_{1-4}$alkoxy or $C_{1-4}$thioalkoxy group, an —$O(CH_2)_nO$— group in which n=1 or 2, an $NO_2$ group, an $NHSO_2R4$ group, an NHR5 group, an OH group, a $C_{1-4}$haloalkyl group, a CN group, a $C_{1-4}$alkoxycarbonyl group, a $C_{1-4}$alkylcarbonyl group, a $C_{1-4}$hydroxyalkyl group and a benzyl or phenyl substituent optionally substituted by a $C_{1-4}$alkoxy or a $C_{1-4}$alkyl group or a halogen atom, or R3 constitutes a ring fused with the benzene ring carrying it, selected from the group composed of a naphthalene, an indole, a benzimidazole, a carbostyril, a benzoxazolone and a benzimidazolone.

R4 represents a $C_{1-4}$alkyl group or a $C_{1-4}$dialkylamino group or a $C_{1-4}$-alkoxyalkyl group or a $C_{1-4}$dialkylaminoalkyl group or a phenyl or phenyl-$C_{1-4}$alkyl group, R5 represents a hydrogen atom or a $C_{1-4}$alkylcarbonyl group or a $C_{1-4}$alkoxy-carbonyl group, and also their pharmaceutically acceptable salts.

According to the invention, compounds of the general formula (I) are those wherein:
R1 represents one or more identical or different substituent(s) selected from the group composed of a $C_{1-4}$alkoxy group, an OH group and an —$O(CH_2)_nO$— group in which n=1 or 2.

According to the invention, compounds of the general formula (I) are those wherein:
R2 represents a hydrogen atom.

According to another embodiment of the invention, compounds of the general formula (I) are those wherein R3 represents a hydrogen atom when A and/or B represent a nitrogen atom.

According to the invention, compounds of the general formula (I) are those wherein:
A and B simultaneously represent a carbon atom.

According to the invention, compounds of the general formula (I) are those wherein:
R3 represents one or more identical or different substituent(s) selected from the group composed of: a halogen atom, a $C_{1-4}$alkoxy group, an —$O(CH_2)_nO$— group in which n=1 or 2, an $NHSO_2R4$ group, an OH group and a CN group.

According to another embodiment of the invention, compounds of the general formula (I) are those wherein:
R3, together with the benzene ring carrying it, represents an indole group or a benzimidazole group or a carbostyril group.

According to another embodiment of the invention, compounds of the general formula (I) are those wherein:
R1 represents one or two identical or different substituents which each represent, independently, a methoxy group, or an —$O(CH_2)_nO$— group in which n=1 or an OH group.

R2 represents a hydrogen atom

A represents a carbon atom and B represents a nitrogen atom or a carbon atom

When A and B represent a carbon atom:
R3 represents one or two identical or different substituent(s) selected from the group composed of: a hydrogen atom, a CN group, a chlorine atom, a fluorine atom, an OH group, an NO$_2$ group, an NHSO$_2$R4 group, an NHR5 group, a CF$_3$ group, a methoxy group, or R3 constitutes a ring fused with the benzene ring carrying it selected from the group composed of: benzimidazole, benzoxazolone, indole, benzimidazolone and carbostyril.

When A represents a carbon atom and B represents a nitrogen atom:

R3 represents a hydrogen atom

R4 represents a methyl group, or an ethyl group, or a dimethylaminoethyl group or an ethoxymethyl group.

R5 represents a hydrogen atom, a COCH$_3$ group or a COOCH$_3$ group

The following are examples of compounds according to the invention:

6,7-dimethoxy-3-{4-[4-(2-methoxyphenyl)-piperazin-1-yl]-butyl}-chromen-4-one
3-{4-[4-(6,7-dimethoxy-4-oxo-4H-chromen-3-yl)-butyl]-piperazin-1-yl}-benzonitrile
3-{4-[4-(2,3-dichlorophenyl)-piperazin-1-yl]-butyl}-6,7-dimethoxychromen-4-one
3-{4-[4-(3-hydroxyphenyl)-piperazin-1-yl]-butyl}-6,7-dimethoxychromen-4-one
6,7-dimethoxy-3-[4-(4-pyrimidin-2-yl-piperazin-1-yl)-butyl]-chromen-4-one
6,7-dimethoxy-3-[4-(4-pyridin-2-yl-piperazin-1-yl)-butyl]-chromen-4-one
3-{4-[4-(2,3-difluorophenyl)-piperazin-1-yl]-butyl}-6,7-dimethoxychromen-4-one
3-{4-[4-(1H-benzimidazol-4-yl-)piperazin-1-yl]-butyl}-6,7-dimethoxychromen-4-one
3-{4-[4-(1H-indol-4-yl)-piperazin-1-yl]-butyl}-6,7-dimethoxychromen-4-one
5-{4-[4-(6,7-dimethoxy-4-oxo-4H-chromen-3-yl)-butyl]-piperazin-1-yl}-1H-quinolin-2-one
6,7-dimethoxy-3-{4-[4-(3-nitrophenyl)-piperazin-1-yl]-butyl}-chromen-4-one
3-{4-[4-(3-aminophenyl)-piperazin-1-yl]-butyl}-6,7-dimethoxychromen-4-one
N-(3-{4-[4-(6,7-dimethoxy-4-oxo-4H-chromen-3-yl)-butyl]-piperazin-1-yl}-phenyl)-methanesulfonamide
N-(3-{4-[4-(6,7-dimethoxy-4-oxo-4H-chromen-3-yl)-butyl]-piperazin-1-yl}-phenyl)-acetamide
methyl (3-{4-[4-(6,7-dimethoxy-4-oxo-4H-chromen-3-yl)-butyl]-piperazin-1-yl}-phenyl)-carbamate
7-{4-[4-(2,3-dichlorophenyl)-piperazin-1-yl]-butyl}-[1,3]dioxolo[4,5-g]chromen-8-one
7-{4-[4-(2,3-difluorophenyl)-piperazin-1-yl]-butyl}-[1,3]dioxolo[4,5-g]chromen-8-one
7-{4-[4-(3-nitrophenyl)-piperazin-1-yl]-butyl}-[1,3]dioxolo[4,5-g]chromen-8-one
7-{4-[4-(3-aminophenyl)-piperazin-1-yl]-butyl}-[1,3]dioxolo[4,5-g]chromen-8-one
N-(3-{4-[4-(8-oxo-8H-[1,3]dioxolo[4,5-g]chromen-7-yl)-butyl]-piperazin-1-yl}-phenyl-acetamide
N-(3-{4-[4-(8-oxo-8H-[1,3]dioxolo[4,5-g]chromen-7-yl)-butyl]-piperazin-1-yl}-phenyl)-methanesulfonamide
N-(3-{4-[4-(8-oxo-8H-[1,3]dioxolo[4,5-g]chromen-7-yl)-butyl]-piperazin-1-yl}-phenyl)-ethanesulfonamide
2-dimethylaminoethanesulfonic acid (3-{4-[4-(8-oxo-8H-[1,3]dioxolo[4,5-g]chromen-7-yl)-butyl]-piperazin-1-yl}-phenyl)-amide
2-methoxyethanesulfonic acid (3-{4-[4-(8-oxo-8H-[1,3]dioxolo[4,5-g]chromen-7-yl)-butyl]-piperazin-1-yl}-phenyl)-amide
7-{4-[4-(1H-indol-4-yl)-piperazin-1-yl]-butyl}-[1,3]dioxolo[4,5-g]chromen-8-one
3-{4-[4-(3-trifluoromethylphenyl)-piperazin-1-yl]-butyl}-6,7-dimethoxychromen-4-one
6-methoxy-3-[4-(4-phenyl-piperazin-1-yl)-butyl]-chromen-4-one
6-methoxy-3-{4-[4-(2-methoxyphenyl)-piperazin-1-yl]-butyl}-chromen-4-one
6-methoxy-3-{4-[4-(3-trifluoromethylphenyl)-piperazin-1-yl]-butyl}-chromen-4-one
7-{4-[4-(2,3-dichlorophenyl)piperazin-1-yl]-butyl}-6-methyl-[1,3]dioxolo[4,5-g]chromen-8-one
6,7-methoxy-7,6-hydroxy-3-{4-[4-(2-methoxyphenyl)-piperazin-1-yl]-butyl}-chromen-4-one
7-{4-[4-(6,7-dimethoxy-4-oxo-4H-chromen-3-yl)-butyl]-piperazin-1-yl}-3H-benzoxazol-2-one
4-{4-[4-(6,7-dimethoxy-4-oxo-4H-chromen-3-yl)-butyl]-piperazin-1-yl}-1,3-dihydrobenzimidazol-2-one The invention relates also to pharmaceutically acceptable salts thereof, as well as to pharmaceutical compositions containing them, and to their use as medicaments intended for the treatment of disorders of the central nervous system.

The present invention relates also to a process for the preparation of those compounds.

The compounds of the general formula 1 are prepared according to scheme 1.

Scheme 1

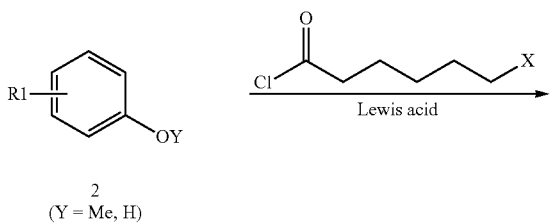

2
(Y = Me, H)

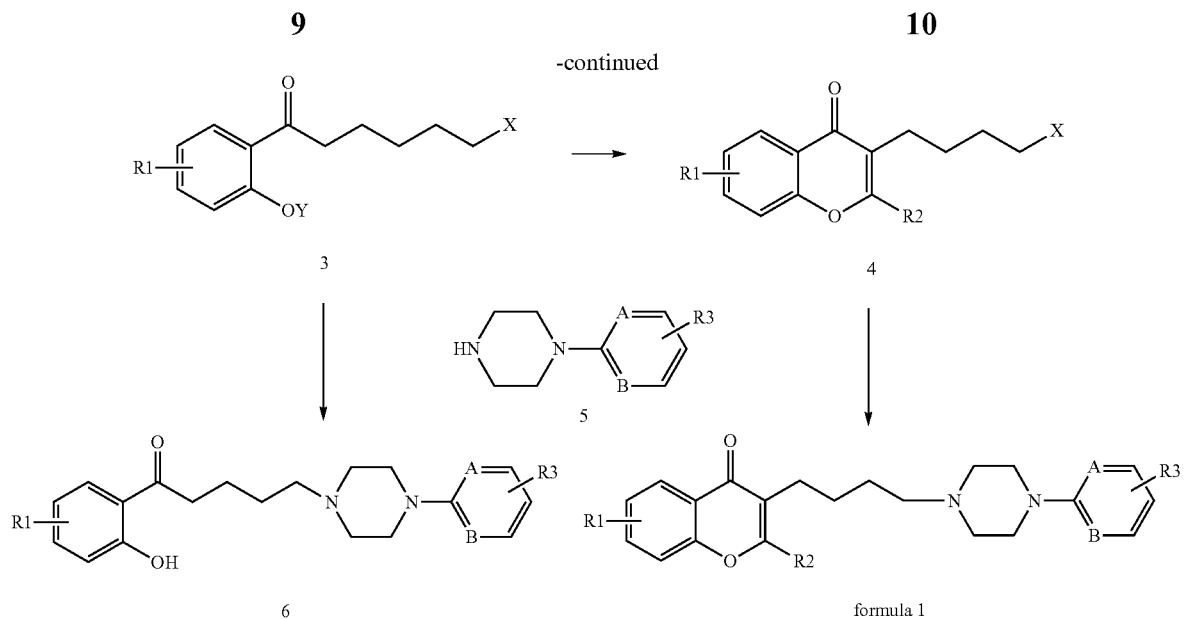

A Friedel-Crafts reaction, or Fries reaction with a substituted aromatic methoxy compound 2 (Y=Me), or substituted phenol compound 3 (Y=H) yields an aromatic ketone 3 (Y=Me, H). That reaction uses an omega halogenated hexanoic acid halide, such as 6-bromohexanoyl chloride. Condensation takes place with or without solvent in the presence of a Lewis acid, such as AlCl3, according to a method analogous to that described in *Chem. Ber.* 1939, 72, 1414, or *J. Org. Chem.* 1955, 20, 38 with chloro or bromoacetyl chloride or bromide. Here, the reaction uses bromohexanoyl chloride, which is condensed in the ortho position of the phenol function to form derivative 3. Where a solvent is employed, a chlorinated solvent, such as methylene chloride, can be used for a reaction at ambient temperature or low temperature or, for a reaction at higher temperature, dichloroethane or 1,1-2,2-tetrachloroethane, for example, may be used. The phenols used with the corresponding substituents are either commercially available, or known from the literature and prepared by demethylation in the presence of agents conventionally employed to demethylate aromatic methoxy compounds, such as HBr and Lewis acids (AlCl$_3$, BBr$_3$). The Friedel Crafts reaction can also be carried out on a methoxylated aromatic ring rich in electrons. The demethylation step yielding the intermediate 3 can take place after the acylation step. The phenol 3 (Y=H), thus acylated, can be cyclised with the acetal of dimethylformamide (=DMF) or of dimethylamine (=DMA), with heating, to yield a halogenated chromone 4. That cyclisation to form a chromone can also be carried out in DMF in the presence of PCl$_5$ and etherate of BF$_3$, as well as with ethyl formate in the presence of sodium according to *Bull. Soc. Chim. Fr.* 1944, 5, 302. The halobutyl chromone derivative 4 is then brought together with substituted arylpiperazines or heteroarylpiperazines of formula 5 in standard manner in the presence of a base such as K$_2$CO$_3$ or caesium carbonate in acetonitrile or methyl ethyl ketone to yield derivatives of formula 1. That procedure is used with piperazines of formula 5 wherein A, B and R3 are as defined hereinabove. A variant of the process can be used and comprises introducing the piperazine moiety prior to the formation of the chromone ring: thus, the condensation of the piperazine of formula 5 with the halogenated phenol of formula 3 under the same conventional alkylation conditions in basic medium (K$_2$CO$_3$/CH$_3$CN or methyl ethyl ketone) to yield compounds of formula 6. The formation of the chromone ring can then be carried out by cyclisation with DMF or the acetal of DMF or of DMA. Using that method, introducing piperazine prior to cyclisation to the chromone, allows a purer cyclised compound to be obtained than by the method of forming the chromone starting from derivative 3 (Y=H). In fact, the heating conditions for cyclisation with DMF at elevated temperature generate dimethylamine which may react with the halogenated derivative 3, yielding a secondary product (formula 4, X=NMe$_2$), and requires an additional purification. The person skilled in the art will be able to select a suitable method according to the substituents carried by the phenylpiperazine 5. Modifications of the piperazine substituents can also be made in the last steps, such as, for example, using piperazine of formula 5 (A=B=C, R3=3-NO$_2$). Reduction of the nitro group in the product of formula 1 (A=B=C, R3=3-NO$_2$) is conventionally effected by catalytic reduction with hydrogen using palladium-on-carbon or Raney nickel, or by treatment with a metal such as iron in acid medium, to yield the corresponding aniline (formula 1, A=B=C, R3=3—NH$_2$). The aniline group can thus be acylated in the presence of pyridine or another base with acetyl chloride, yielding the acetamide derivative, with methyl chloroformate, yielding the methyl carbamate, or with methanesulfonyl chloride, yielding the methylsulfonamide. The reaction of the chloroethylsulfonyl chloride can be carried out in the same manner, and then the vinyl intermediate obtained can be brought together with dimethylamine or with sodium methoxide to yield, respectively, a dimethylaminoethylsulfonamide or methoxyethylsulfonamide substituent. The literature mentions heterocyclic arylpiperazines, such as 4-piperazin-1-yl-1H-indole, 4-piperazin-1-yl-1H-benzimidazole, 7-piperazin-1-yl-3-H-benzoxazol-2-one, 4-piperazin-1-yl-1,3-dihydrobenzimidazol-2-one, 5-piperazin-1-yl-1H-quinolin-2-one. Heterocyclic piperazines can be prepared by reaction of the corresponding anilines with nitrogen mustards (bischloroethylamines). Those nitrogen mustards can be N-substituted by a benzyl protecting group, which is removable by simple hydrogenolysis with Pd/C under hydrogen when the condensation with piperazine has been effected (Fr2504532; Fr2524884; Bioorg. Med. Chem. Lett. 1998, 8, 2675; Bioorg. Med. Chem.

Let. 2001, 11, 2345, J. Med. Chem. 2002, 45, 4128; J. Med. Chem. 2004, 47, 871; Synth. Commun. 2006, 36, 1983; Synthesis 1977, 33; Tet. Let. 1970, 5265; Chem. Pharm. Bull. 1981, 29, 651 or 1979, 27, 2627; Tet. 2000, 56, 3245).

The invention thus relates also to the following preparation processes:

Process for the preparation of compounds of the general formula 1, characterised in that an optionally substituted chromone of formula 4 (X=Cl, Br, I) is prepared, which is reacted with a piperazine of formula 5.

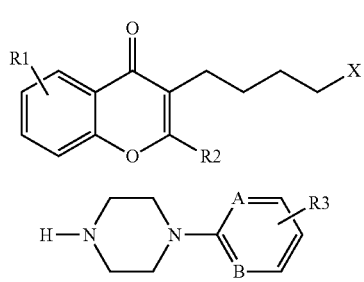

Formula 4

Formula 5

The radicals R1, R2, R3, A and B have the meanings given hereinbefore.

Process for the preparation of compounds of the general formula 1, characterised in that an optionally substituted phenol derivative of formula 6 is prepared starting from a compound of formula 3 (X=Cl, Br), and is reacted with DMF (=dimethylformamide) or the dimethylacetal of DMF or of DMA (=dimethylamine).

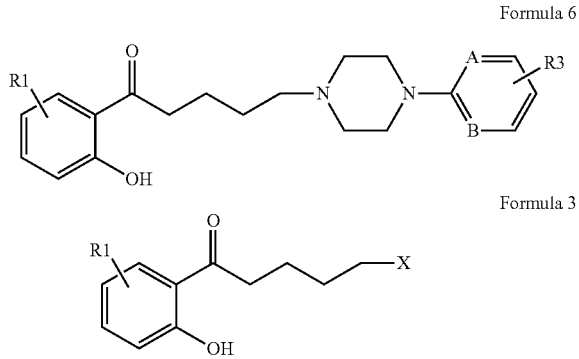

Formula 6

Formula 3

The radicals R1, R3, A and B have the meanings given hereinbefore, under alkylation conditions in the presence of a base such as $K_2CO_3$, $Cs_2CO_3$ or $NEt_3$, in a solvent such as acetonitrile or methyl ethyl ketone.

The invention relates also to a pharmaceutical composition comprising at least one compound of the general formula (I) or a pharmaceutically acceptable salt thereof and a pharmaceutically acceptable excipient.

Given the selective modulation of the transmissions of dopamine exerted by the receptor DRD3 in the limbic regions, which are implicated in emotive and cognitive processes, the compounds of the invention are suitable in various therapeutic applications and do not interfere with dopaminergic transmissions of the extra-pyramidal, antehypophysial or vegetative systems (for example the area postrema). The compounds of the invention can thus be used for the preparation of pharmaceutical compositions and medicaments for the treatment of neurological or psychiatric disease, conditions or disorders involving the DRD3 receptor, such as psychotic states.

Furthermore, since an effect of antidepressant medicaments is to increase the expression of the DRD3 receptor in regions of the brain involved in motivation, the compounds of the invention are able to imitate the action of antidepressant medicaments. The compounds can thus be employed for the preparation of pharmaceutical compositions and medicaments for the treatment of depression.

Given the role of the DRD3 receptor in drug-dependence states, pharmaceutical compositions or medicaments based on the compounds described in the present invention may usefully be administered in states associated with abstinence and/or to facilitate the detoxification of individuals dependent on cocaine, heroin, alcohol, tobacco, and other addictive substances.

The compounds according to the invention, like partial agonists of the DRD3 receptor generally, may also be employed as a supplementary treatment to the treatment of Parkinson's disease with L-DOPA.

The compounds according to the invention, like partial agonists and antagonists of the DRD3 receptor generally, may also be employed for the treatment of essential tremor.

Accordingly, compounds of formula 1, bases or salts, can be used for the treatment of neurological or psychiatric conditions, especially conditions that can be treated by DRD3 receptor agonists, partial agonists or antagonists.

The invention relates also to a method of treating neurological or psychiatric conditions, diseases or disorders that comprises administering a compound of formula 1 in a therapeutically effective amount to a patient requiring treatment. The invention relates in addition to compounds of formula 1 for their use as medicaments.

The invention relates also to compounds of formula 1 for the manufacture of a medicament for the treatment of a neurological or psychiatric disease or disorder or erectile dysfunction or dependence on drugs or on addictive substances.

The invention relates to compounds of the general formula (I) for the manufacture of a medicament for the treatment of Parkinson's disease, psychosis, schizophrenia, dyskinesias associated with Parkinson's disease, cognitive deficiency optionally associated with age or with Alzheimer's disease, mood disorder, essential tremor, anxiety, depression, bipolar disorder, sexual impotence, premature ejaculation, alcoholism and nicotine addiction.

Compounds of formula 1 according to the invention can be administered by the oral, systemic, parenteral, nasal or rectal route. The compound can especially be administered by the oral route in an appropriate formulation. The dosages of the compounds of formula 1 in the compositions of the invention can be adjusted to obtain an amount of active substance that is effective in obtaining the desired therapeutic response for a composition peculiar to the method of administration. The dosage level chosen depends therefore on the desired therapeutic effect, the administration route, the desired duration of treatment and other factors.

Compounds of formula 1 were evaluated in vitro as DRD3 ligands and modulators of the activity of that receptor in accordance with the invention in cells expressing human recombinant DRD3 receptor. The inhibition constants (KO were measured by inhibition of the binding of [$^3$H]spiperone as described by Cussac et al., in *Naunyn-Schmiedeberg's Arch. Pharmacol.* 2000, 361, 569. The inventors demonstrated that the compounds of formula 1 behave as potent ligands, with $K_i$ values from 0.1 to 30 nanomole·liter$^{-1}$. Those same compounds exhibit a noticeable affinity for the D2 receptor of dopamine that is from 10 to 200 times weaker. Compounds of formula 1 were evaluated for their agonist, partial agonist, or antagonist activity by using the MAP-kinase activity test on human recombinant receptors described in Cussac D. et al., *Mol. Pharmacol.* 1999, 56, 1025-1030. The intrinsic activities of the compounds of formula 1 are between 0 (antagonist) and 0.80 (agonist).

Compounds of formula 1 were evaluated in vivo in the test of hyperactivity induced by MK-801 in the mouse (Leriche L. et al., *Neuropharmacology* 2003, 45, 174). The $ED_{50}$ values of compounds of formula 1 are between 0.01 and 6 mg/kg.

The total daily dose of the compounds for use in accordance with this invention, administered in single or divided doses, may be in amounts of, for example, from 0.001 to approximately 100 mg/kg body weight daily.

The specific dose level for any particular patient will depend on a variety of factors, including body weight, general health, sex, diet, duration and route of administration, levels of intestinal absorption and resorption and of excretion, combination with other medicaments and the severity of the particular condition being treated.

By way of example, but in a non-limiting manner, the preparations of the compounds of the invention are illustrated in the following Examples:

EXAMPLE 1

6,7-Dimethoxy-3-{4-[4-(2-methoxyphenyl)-piperazin-1-yl]-butyl}-chromen-4-one

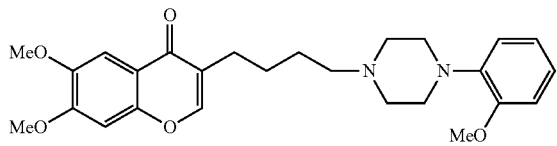 [SMILES: COc1cc2occ(CCCCN3CCN(c4ccccc4OC)CC3)c(=O)c2cc1OC]

Step 1:
6-bromo-1-(2,4,5-trimethoxyphenyl)-hexan-1-one

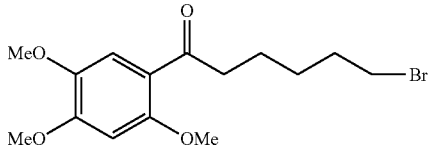 [SMILES: COc1cc(OC)c(C(=O)CCCCCBr)cc1OC]

6 ml (40 mmol) of 1,2,4-trimethoxybenzene are introduced into 80 ml of dry $CH_2Cl_2$ and the mixture is cooled to −10° C. with stirring. 6-Bromohexanoyl chloride (6.2 ml, 40 mmol) dissolved in 20 ml of $CH_2Cl_2$ is then added dropwise. $AlCl_3$ (5.6 g, 42 mmol) is progressively introduced in small portions into the reaction mixture. The reaction is maintained with stirring for 8 h with a return to ambient temperature. The reaction mixture is then poured onto ice (200 ml) and acidified to pH 1 using HCl. The mixture is stirred until it returns to ambient temperature, 1 h. After evaporation of the $CH_2Cl_2$, the mixture is extracted with AcOEt, and the organic phases are separated, dried over $MgSO_4$, filtered and evaporated. The residue is subjected to flash chromatography over $SiO_2$ with a gradient of pure heptane to heptane-AcOEt 50-50. The pure fractions are evaporated to obtain 13.6 g (yield=99%) of crystals. TLC $SiO_2$ (heptane-ACOEt 70-30) Rf=0.5; $^1H$ NMR ($CDCl_3$): 7.41 (s, 1H), 6.50 (s, 1H), 3.95 (s, 3H), 3.91 (s, 3H), 3.87 (s, 3H), 3.43 (t, 2H, J=6.76 Hz), 2.98 (t, 2H, J=6.32 Hz), 1.91 (m, 2H), 1.71 (m, 2H), 1.51 (m, 2H).

Step 2: 6-Bromo-1-(2-hydroxy-4,5-dimethoxyphenyl)-hexan-1-one

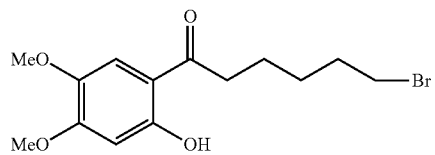 [SMILES: COc1cc(O)c(C(=O)CCCCCBr)cc1OC]

13.6 g of the product obtained in the above Step are dissolved in 80 ml of 48% HBr. The mixture is heated at 90° C. for 5 h. The reaction mixture is then poured onto ice (300 ml) and extracted with AcOEt. The organic phases are separated, dried over $MgSO_4$, filtered and evaporated to obtain a green oil, which is subjected to flash chromatography over $SiO_2$ with a gradient of pure heptane to heptane-AcOEt 85-15. 7.33 (yield=56%) of 6-bromo-1-(2-hydroxy-4,5-dimethoxyphenyl)-hexan-1-one are obtained, $^1H$ NMR ($CDCl_3$): 12.7 (s, 1H), 7.08 (s, 1H), 6.46 (s, 1H), 3.91 (s, 3H), 3.87 (s, 3H), 3.44 (t, 2H, J=8 Hz), 2.92 (t, 2H, J=7.2 Hz), 1.93 (m, 2H), 1.78 (m, 2H), 1.55 (m, 2H); and also 1.4 g of the di-demethylated compound, 6-bromo-1-(2,4/5-dihydro-5/4-methoxyphenyl) hexan-1-one, $^1H$ NMR ($CDCl_3$): 12.5 (s, 1H), 7.22 (s, 1H), 6.45 (s, 1H), 5.20 (s, 1H), 3.93 (s, 3H), 3.42 (t, 2H, J=6.68 Hz), 2.89 (t, 2H, J=7.32 Hz), 1.91 (m, 2H), 1.76 (m, 2H), 1.53 (m, 2H).

Step 3:
3-(4-Bromobutyl)-6,7-dimethoxychromen-4-one

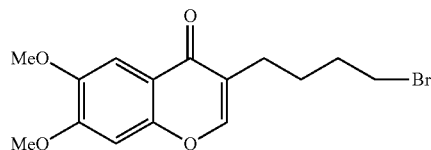 [SMILES: COc1cc2occ(CCCCBr)c(=O)c2cc1OC]

$1^{st}$ method: A solution A is prepared from 500 mg of the compound of the above Step, 6-bromo-1-(2-hydroxy-4,5-dimethoxyphenyl)-hexan-1-one (1.5 mmol), dissolved in 0.60 ml (4.5 mmol) of $Et_2O$—$BF_3$, and the solution is cooled to 10° C. 2.3 ml of DMF are then added. There is prepared, in addition, a solution B of 4 ml of DMF and there is added thereto in small portions at 10° C. 470 mg (2.25 mmol) of $PCl_5$. Solution B is heated at 55° C. for 20 min, and is then introduced dropwise into solution A, referred to at the beginning, with a return to ambient temperature. The mixture turns orangey yellow and precipitates. 50 ml of 0.1N HCl are introduced and the mixture is extracted with AcOEt, the organic phases are washed with saturated NaCl solution, separated, dried over $MgSO_4$, filtered and evaporated. The residue is subjected to flash chromatography over $SiO_2$ with a gradient of pure heptane to heptane-AcOEt 70-30. The purified fractions crystallise after evaporation. 300 mg of 3-(4-bromobutyl)-6,7-dimethoxychromen-4-one are obtained in the form of crystals (yield=59%); TLC $SiO_2$hept-AcOEt 50-50 Rf=0.4.

2nd method: A solution of 500 mg (1.5 mmol) of the compound of the above Step, 6-bromo-1-(2-hydroxy-4,5-dimethoxyphenyl)-hexan-1-one, in 30 ml of dry toluene is refluxed, with stirring, with 0.6 ml (4.5 mmol) of DMF dimethylacetal. Reflux is continued for 5 h. After concentration, and purification by flash chromatography with a gradient of pure heptane to heptane-ACOEt 80-20, 270 mg (yield=53%) of 3-(4-bromobutyl)-6,7-dimethoxychromen-4-one are obtained, after evaporation, in the form of white crystals identical to those obtained by the 1st method. TLC SiO₂ hept-AcOEt 70-30 Rf=0.3. ¹H NMR (DMSO): 8.19 (s, 1H), 7.36 (s, 1H), 7.16 (s, 1H), 3.89 (s, 3H), 3.84 (s, 3H), 3.65 (t, 2H, J=6.3 Hz), 2.38 (t, 2H, J=7.3 Hz), 1.72 (m, 2H), 1.64 (m, 2H), 1.55 (m, 2H).

Step 4: 6,7-Dimethoxy-3-{4-[4-(2-methoxyphenyl)-piperazin-1-yl]-butyl}-chromen-4-one

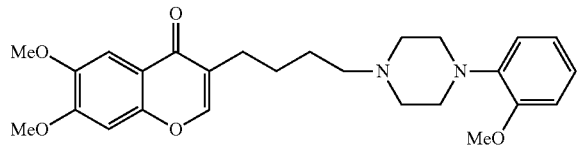 [SMILES: COc1cc2occ(CCCCN3CCN(c4ccccc4OC)CC3)c(=O)c2cc1OC]

The brominated derivative obtained in the above Step 3 (150 mg, 0.44 mmol) is suspended in 10 ml of methyl ethyl ketone, and 120 mg (0.62 mmol) of 2-methoxyphenylpiperazine and 121 mg (0.87 mmol) of K₂CO₃, as well as 10 mg of tetrabutylammonium bromide, are added. The mixture is refluxed for 20 h and then concentrated. The residue is taken up in water and extracted with ethyl acetate. The organic phases are separated, dried over MgSO4, filtered and evaporated to yield a colourless oil. Flash chromatography over SiO2 eluted with a gradient of CH₂Cl₂ to CH₂Cl₂-MeOH 90-10 allows an oil to be obtained which crystallises in iPr₂O. 128 mg (yield=60%) of white crystals are obtained. M.p. ° C.=124-130; MS (ESI) m/z=453 (MH+); ¹H NMR (CDCl3): 7.72 (s, 1H), 7.55 (s, 1H), 6.92 (m, 5H), 3.97 (s, 3H), 3.86 (s, 3H), 3.12 (m, 4H), 2.69 (m, 4H), 2.49 (m, 4H), 1.64 (m, 4H).

The products of the following Examples are obtained by the same sequence of reactions:

EXAMPLE 2

3-{4-[4-(6,7-Dimethoxy-4-oxo-4H-chromen-3-yl)-butyl]-piperazin-1-yl}-benzonitrile

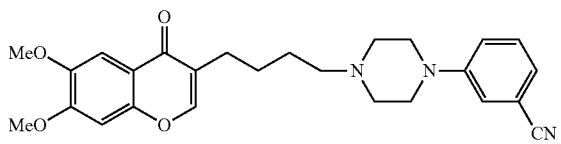 [SMILES: COc1cc2occ(CCCCN3CCN(c4cccc(C#N)c4)CC3)c(=O)c2cc1OC]

By condensation of the brominated derivative, 3-(4-bromobutyl)-6,7-dimethoxychromen-4-one, obtained in Step 3 of Example 1 with 3-cyanophenyl-piperazine, 3-{4-[4-(6,7-dimethoxy-4-oxo-4H-chromen-3-yl)-butyl]-piperazin-1-yl}-benzonitrile is obtained in a yield of 40%. M.p. ° C.=154-155; analytical HPLC Sym C8, 4.6×250 mm, 5μ, eluant: CH₃CN—H₂O, KH₂PO₄ 30-70-6.8 g/l, pH4, r.t.=9.72 min; MS ESI, m/z=448 (MH+); ¹H NMR (DMSO): 8.17 (s, 1H), 7.13-7.39 (m, 6H), 3.89 (s, 3H), 3.84 (s, 3H), 3.19 (m, 4H), 2.47 (m, 4H), 2.38 (t, 2H, J=6.8 Hz), 2.32 (t, 2H, J=6.8 Hz), 1.50 (m, 4H).

EXAMPLE 3

3-{4-[4-(2,3-Dichlorophenyl)-piperazin-1-yl]-butyl}-6,7-dimethoxychromen-4-one

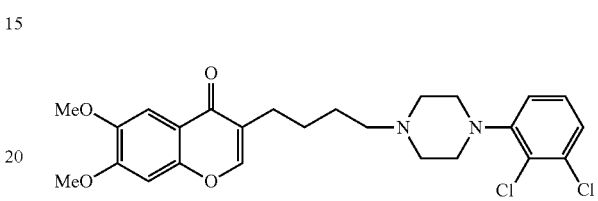

In a similar manner to Example 1, but using 2,3-dichlorophenylpiperazine, 3-{4-[4-(2,3-dichlorophenyl)-piperazin-1-yl]-butyl}-6,7-dimethoxychromen-4-one is obtained in a yield of 62%. M.p. ° C.=160-162; analytical HPLC Sym C8, 4.6×250 mm, 5μ, eluant: CH₃CN—H₂O, KH₂PO₄ 40-60-6.8 g/l, pH4, r.t.=8.80 min; MS ESI, m/z=491; ¹H NMR (CDCl3): 7.72 (s, 1H), 7.55 (s, 1H), 7.14 (m, 2H), 6.95 (m, 1H), 6.83 (s, 1H), 3.97 (s, 6H, OCH3), 3.07 (m, 4H), 2.64 (m, 4H), 2.48 (m, 4H), 1.64 (m, 4H).

Preparation of the hydrochloride: 2.64 g of the base obtained above are dissolved in a mixture of 100 ml of acetone-MeOH (50-50). A solution of isopropanol, 2N HCl, is added. The precipitated salt is filtered off to obtain, after drying in vacuo, 2.02 g of the hydrochloride (yield=72%). M.p. ° C.=252-254.

EXAMPLE 4

3-{4-[4-(3-Hydroxyphenyl)-piperazin-1-yl]-butyl}-6,7-dimethoxychromen-4-one

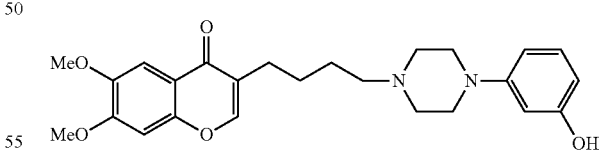

Using the same starting material, 3-(4-bromobutyl)-6,7-dimethoxychromen-4-one obtained in Step 3 of Example 1, but with 3-hydroxyphenylpiperazine, and using a microwave reaction vessel (15 min, 160° C., 150 w), 3-{4-[4-(3-hydroxyphenyl)-piperazin-1-yl]-butyl}-6,7-dimethoxychromen-4-one is obtained in a similar manner to Example 1 in a yield of 17%. M.p. ° C.=177-180; analytical HPLC Sym C8, 4.6×250 mm, 5μ, eluant: CH₃CN—H₂O, KH₂PO₄ 25-75-6.8 g/l, pH4, r.t.=9.99 min; MS ESI, m/z=439 (MH+); ¹H NMR (CDCl3): 7.72 (s, 1H), 7.55 (s, 1H), 7.09 (t, 1H, J=8 Hz), 6.83 (s, 1H), 6.49 (d, 1H, J=8.28 Hz), 6.39 (s, 1H), 6.31 (d, 1H, J=7.84 Hz), 3.97 (s, 6H, OCH3), 3.18 (m, 4H), 2.58 (m, 4H), 2.49 (m, 2H), 2.43 (m, 2H), 1.62 (m, 4H).

EXAMPLE 5

6,7-Dimethoxy-3-[4-(4-pyrimidin-2-yl-piperazin-1-yl)-butyl]-chromen-4-one

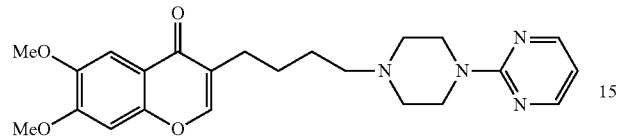

In a similar manner to Example 1, but using 2-pyrimidinylpiperazine, 6,7-dimethoxy-3-[4-(4-pyrimidin-2-yl-piperazin-1-yl)-butyl]-chromen-4-one is obtained in a yield of 77%. M.p. ° C.=123-124; analytical HPLC Sym C8, 4.6×250 mm, 5µ, eluant: $CH_3CN$—$H_2O$, $KH_2PO_4$ 20-80-6.8 g/l, pH4, r.t.=14.31 min; MS ESI, m/z=425 (MH+); $^1$H NMR ($CDCl_3$): 8.34 (d, 2H, J=4.64 Hz), 8.17 (s, 1H), 7.36 (s, 1H), 7.15 (s, 1H), 6.60 (t, 1H, J=4.6 Hz), 3.89 (s, 3H), 3.84 (s, 3H), 3.69 (m, 4H), 2.38 (m, 6H), 2.31 (m, 2H), 1.51 (m, 4H).

EXAMPLE 6

6,7-Dimethoxy-3-[4-(4-pyridin-2-yl-piperazin-1-yl)-butyl]-chromen-4-one

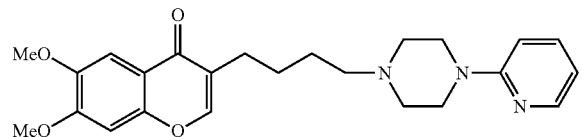 [SMILES: COc1cc2occ(CCCCN3CCN(c4ccccn4)CC3)c(=O)c2cc1OC]

In a similar manner to Example 1, but using 2-pyridinylpiperazine, 6,7-dimethoxy-3-[4-(4-pyridin-2-yl-piperazin-1-yl)-butyl]-chromen-4-one is obtained in a yield of 50%. M.p. ° C.=41-143; analytical HPLC XBridge, 4.6×250 mm, 8.5µ, eluant: $CH_3CN$—$H_2O$, $KH_2PO_4$ 20-80-6.8 g/l, pH4, r.t.=14.21 min; MS ESI, m/z=424 (MH+); $^1$H NMR (DMSO): 8.17 (s, 1H), 8.09 (d, 1H, J=4.28 Hz), 7.5 (t, 1H, J=7.6 Hz), 7.36 (s, 1H), 7.15 (s, 1H), 6.79 (d, 1H, J=8.6 Hz), 6.61 (t, 1H, J=5.8 Hz), 3.89 (s, 3H), 3.84 (s, 3H), 3.43 (m, 4H), 2.39 (m, 6H), 2.33 (m, 2H), 1.51 (m, 4H).

EXAMPLE 7

3-{4-[4-(2,3-Difluorophenyl)-piperazin-1-yl]-butyl}-6,7-dimethoxychromen-4-one,

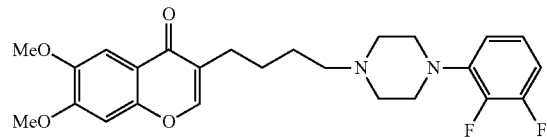 [SMILES: COc1cc2occ(CCCCN3CCN(c4cccc(F)c4F)CC3)c(=O)c2cc1OC]

In a similar manner to Example 1, but using 2,3-difluorophenylpiperazine described in J. Med. Chem. 2006, 49, 3628, 3-{4-[4-(2,3-difluorophenyl)-piperazin-1-yl]-butyl}-6,7-dimethoxychromen-4-one is obtained in a yield of 33%. M.p. ° C.=148-151; Anal: $C_{25}H_{28}N_2O_4F_2$=458.51, calc C, % 65.49; H, % 6.16; N, % 6.11. found C, % 65.44; H, % 6.29; N, % 6.26. MS ESI, m/z=459 (MH+); $^1$H NMR (DMSO): 8.18 (s, 1H), 7.36 (s, 1H), 7.16 (s, 1H), 7.08 (dd, 1H, J=14.4 Hz, J'=6.8 Hz), 6.96 (dd, 1H, J=17.2 Hz, J'=8 Hz), 6.83 (t, 1H, J=7.6 Hz), 3.89 (s, 3H), 3.84 (s, 3H), 3.32 (m, 4H), 3.02 (m, 4H), 2.36 (m, 4H), 1.50 (m, 4H).

EXAMPLE 8

3-{4-[4-(1H-Benzimidazol-4-yl-)piperazin-1-yl]-butyl}-6,7-dimethoxychromen-4-one

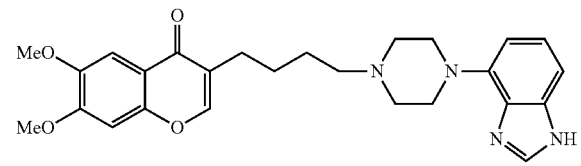

In a similar manner to Example 1, but using 4-benzimidazolyll piperazine described in Tet. 2000, 56, 3245, 3-{4-[4-(1H-benzimidazol-4-yl-)piperazin-1-yl]-butyl}-6,7-dimethoxychromen-4-one is obtained in a yield of 66%. M.p. ° C.=175-179; analytical HPLC XBridge, 4.6×250 mm, 8.5µ, eluant: $CH_3CN$—$H_2O$, $KH_2PO_4$ 20-80-6.8 g/l, pH4, r.t.=9.41 min; MS ESI, m/z=463 (MH+); $^1$H NMR (DMSO): 12.3 (m, 1H), 8.19 (s, 1H), 8.04 (s, 1H), 7.37 (s, 1H), 7.16 (s, 1H), 7.03 (m, 2H), 6.48 (m, 1H), 3.89 (s, 3H), 3.85 (s, 3H), 3.45 (m, 4H), 3.32 (m, 4H), 2.57 (m, 4H), 2.40 (m, 4H), 1.54 (m, 4H).

EXAMPLE 9

3-{4-[4-(1H-Indol-4-yl)-piperazin-1-yl]-butyl}-6,7-dimethoxychromen-4-one

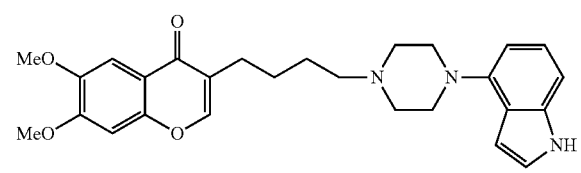 [SMILES: COc1cc2occ(CCCCN3CCN(c4cccc5[nH]ccc45)CC3)c(=O)c2cc1OC]

In a similar manner to Example 1, but using 4-indolyl-piperazine described in J. Med. Chem. 2002, 45, 4128, 3-{4-[4-(1H-indol-4-yl-)piperazin-1-yl]-butyl}-6,7-dimethoxychromen-4-one is obtained in a yield of 69%. M.p. ° C.=197-199; analytical HPLC XBridge, 4.6×250 mm, 8.5µ, eluant: $CH_3CN$—$H_2O$, $KH_2PO_4$ 30-70-6.8 g/l, pH4, r.t.=8.15 min; MS ESI, m/z=462 (MH+); $^1$H NMR (DMSO): 11.0 (m, 1H), 8.19 (s, 1H), 7.37 (s, 1H), 7.22 (m, 1H), 6.96 (m, 2H), 6.43 (m, 1H), 6.35 (m, 1H), 3.89 (s, 3H), 3.85 (s, 3H), 3.09 (m, 4H), 2.57 (m, 4H), 2.40 (m, 4H), 1.54 (m, 4H).

Hydrochloride: M.p. ° C.=244; Anal. $C_{27}H_{31}N_3O_4$, HCl=510.43 (+5.88% $H_2O$) calc. C, % 63.26; H, % 6.37; N, % 8.20. found C, % 62.95; H, % 6.15; N, % 7.98.

EXAMPLE 10

5-{4-[4-(6,7-Dimethoxy-4-oxo-4H-chromen-3-yl)-butyl]-piperazin-1-yl}-1H-quinolin-2-one

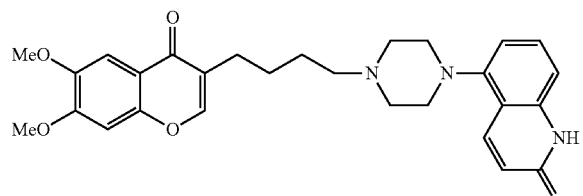

Step 1: 5-Amino-1H-quinolin-2-one

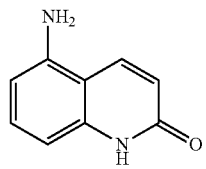 [SMILES: Nc1cccc2[nH]c(=O)ccc12]

A solution of 2.1 g (11 mmol) of 5-nitro-1H-quinolin-2-one (*Chem. Pharm. Bull.* 1981, 29, 651) in 40 ml of AcOH is hydrogenated with 210 mg of 10% Pd/C in the presence of hydrogen for 24 h with vigorous stirring. The catalyst is filtered off and the mixture is evaporated. The residue is subjected to flash chromatography over $SiO_2$ with a gradient of pure $CH_2Cl_2$ to $CH_2Cl_2$-MeOH 99-1. After evaporation, 1.67 g (yield 97%) of yellow crystals are obtained. $^1$H NMR (DMSO): 11.38 (s, 1H), 8.08 (d, 1H, J=8 Hz), 7.10 (t, 1H, J=7.6 Hz), 6.44 (d, 1H, J=8 Hz), 6.33 (d, 1H, J=8 Hz), 6.26 (d, 1H, J=10 Hz), 5.85 (s, 2H).

Step 2: 5-piperazin-1-yl-1H-quinolin-2-one

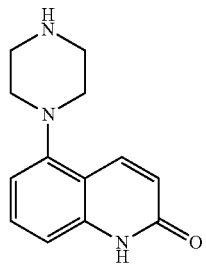 [SMILES: O=c1ccc2c(N3CCNCC3)cccc2[nH]1]

800 mg of the derivative of the above Step (4.96 mmol) are introduced into a microwave reaction vessel with 890 mg (4.96 mmol) of bis-2-chloroethylamine with 1.25 ml of 2-(2-methoxyethoxy)-ethanol and heated at 150° C. for 20 h. After the addition of 1N sodium hydroxide solution, the mixture is extracted with $CH_2Cl_2$. The organic phases are separated, dried over $MgSO_4$, filtered and evaporated. Flash chromatography with a gradient of pure $CH_2Cl_2$ to $CH_2Cl_2$-MeOH—$NH_4OH$ 90-9-1 allows, after evaporation and trituration in ethyl ether, 260 mg (yield=23%) of yellow crystals to be isolated. MS, ESI m/z=230 (MH+); $^1$H NMR (DMSO): 11.67 (s, 1H), 7.99 (d, 1H, J=10 Hz), 7.39 (t, 1H, J=8 Hz), 6.98 (d, 1H, J=8.4 Hz), 6.79 (d, 1H, J=7.6 Hz), 6.45 (d, 1H, J=10 Hz), 2.90 (m, 4H), 2.86 (m, 4H);

Step 3: 5-{4-[4-(6,7-Dimethoxy-4-oxo-4H-chromen-3-yl)-butyl]-piperazin-1-yl}-1H-quinolin-2-one

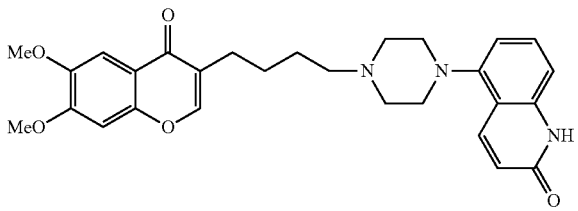 [SMILES: COc1cc2occ(CCCCN3CCN(c4cccc5[nH]c(=O)ccc45)CC3)c(=O)c2cc1OC]

The piperazine obtained in the above Step is then condensed in the same manner as in Step 4 of Example 1 with the brominated derivative 3-(4-bromobutyl)-6,7-dimethoxy-chromen-4-one obtained in Step 3 of Example 1, but using acetonitrile as solvent. 300 mg (yield=54%) of pale yellow crystals are obtained. M.p. ° C.=243-246; analytical HPLC Xbridge C8, 4.6×250 mm, 5µ, eluant: $CH_3CN$—$H_2O$, $KH_2PO_4$ 20-80-6.8 g/l, pH4, r.t.=12.69 min; MS ESI, m/z=490 (MH+).

EXAMPLE 11

6,7-Dimethoxy-3-{4-[4-(3-nitrophenyl)-piperazin-1-yl]-butyl}-chromen-4-one

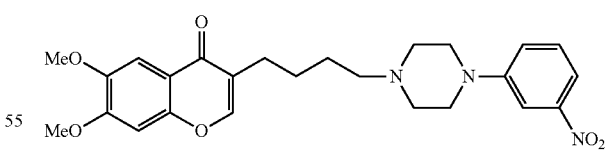

In a similar manner to Example 1, but using 3-nitrophenylpiperazine, 6,7-dimethoxy-3-{4-[4-(3-nitrophenyl)-piperazin-1-yl]-butyl}-chromen-4-one is obtained in a yield of 16%. M.p. ° C.=149-151; analytical HPLC Sym C8, 4.6×250 mm, 5µ, eluant: $CH_3CN$—$H_2O$, $KH_2PO_4$ 30-70-6.8 g/l, pH4, r.t.=12.11 min; MS APCI, m/z=468; $^1$H NMR ($CDCl_3$): 7.72 (s, 1H), 7.71 (d, 1H, J=7.8 Hz), 7.64 (d, 1H, J=8.04 Hz), 7.55

(s, 1H), 7.36 (t, 1H, J=8.2 Hz), 7.17 (d, 1H, J=8.16 Hz), 6.83 (s, 1H), 3.97 (s, 6H), 3.29 (m, 4H), 2.61 (m, 4H), 2.47 (m, 4H), 1.63 (m, 4H).

EXAMPLE 12

3-{4-[4-(3-Aminophenyl)-piperazin-1-yl]-butyl}-6,7-dimethoxychromen-4-one

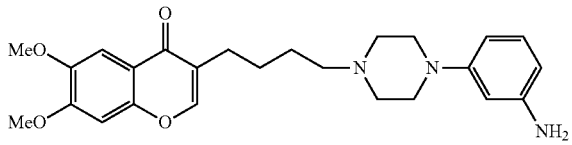 [SMILES: COc1cc2occ(CCCCN3CCN(c4cccc([N+](=O)[O-])c4)CC3)c(=O)c2cc1OC]

The nitro compound of the above Example 11 (910 mg, 1.95 mmol) is hydrogenated in a mixture of 50 ml of CH$_2$Cl$_2$ and 50 ml of EtOH with 91 mg of 10% Pd/C under a hydrogen atmosphere for 24 h with vigorous stirring. After removal of the catalyst by filtration and after evaporation, 720 mg of pink crystals are isolated. Flash chromatography over SiO2, eluted with a gradient of pure CH$_2$Cl$_2$ to CH$_2$Cl$_2$-MeOH 95-5, allows 550 mg (yield=64%) of beige crystals to be isolated by trituration with iPr$_2$O. M.p. °C.=175-176; analytical HPLC Xbridge C8, 4.6×250 mm, 5μ, eluant: CH3CN—H$_2$O, KH2PO4 20-80-6.8 g/l, pH4, r.t.=11.46 min; MS ESI, m/z=438 (MH+).

EXAMPLE 13

N-(3-{4-[4-(6,7-Dimethoxy-4-oxo-4H-chromen-3-yl)-butyl]-piperazin-1-yl}-phenyl)-methanesulfonamide

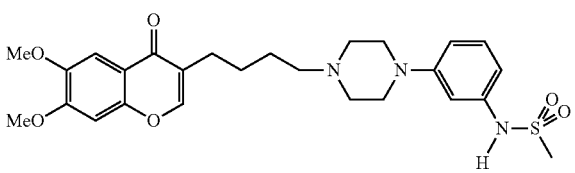 [SMILES: COc1cc2occ(CCCCN3CCN(c4cccc(NS(C)(=O)=O)c4)CC3)c(=O)c2cc1OC]

427 mg (0.98 mmol) of the compound 3-{4-[4-(3-aminophenyl)-piperazin-1-yl-]-butyl}-6,7-dimethoxychromen-4-one obtained in the above Example 12 are suspended in 10 ml of CH$_2$Cl$_2$, 0.16 ml (1.95 mmol) of pyridine is added and, at 0° C., 75 μl (0.98 mmol) of mesyl chloride dissolved in 2 ml of CH$_2$Cl$_2$ are added dropwise. Stirring is maintained at ambient temperature for 8 h. The mixture is poured into water and extracted with CH$_2$Cl$_2$. The organic phases are separated, dried over MgSO$_4$, filtered and evaporated. The residue is subjected to flash chromatography over SiO$_2$ and eluted with a gradient of CH$_2$Cl$_2$ to CH$_2$Cl$_2$-MeOH 90-10. After evaporation, the oil obtained is crystallised in iPr2O to obtain 272 mg of beige crystals (yield=54%). M.p. °C.=186-189; analytical HPLC Xbridge C8, 4.6×250 mm, 51.1, eluant: CH3CN—H2O, KH2PO4 30-70-6.8 g/l, pH4, r.t.=6.91 min; MS ESI, m/z=516 (MH+); $^1$H NMR (CDCl3): 7.72 (s, 1H), 7.55 (s, 1H), 7.19 (t, 1H, J=8.2 Hz), 6.83 (s, 1H), 6.78 (s, 1H), 6.73 (d, 1H, J=8.52 Hz), 6.63 (d, 1H, J=7.4 Hz), 6.29 (m, 1H), 3.97 (s, 6H), 3.19 (m, 4H), 2.99 (s, 3H), 2.59 (m, 4H), 2.49 (m, 2H), 2.44 (m, 2H), 1.59 (m, 4H).

EXAMPLE 14

N-(3-{4-[4-(6,7-Dimethoxy-4-oxo-4H-chromen-3-yl)-butyl]-piperazin-1-yl}-phenyl)-acetamide

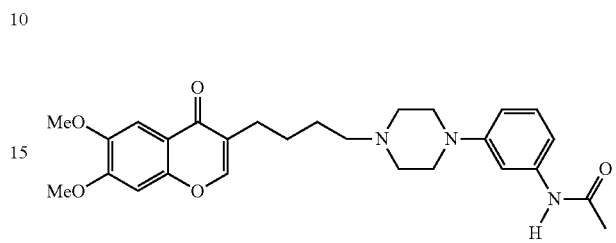

In a similar manner to Example 13, but using acetyl chloride and 3-{4-[4-(3-aminophenyl)-piperazin-1-yl]-butyl}-6,7-dimethoxychromen-4-one obtained in Example 12, N-(3-{4-[4-(6,7-dimethoxy-4-oxo-4H-chromen-3-yl)-butyl]-piperazin-1-yl}-phenyl)-acetamide is obtained.

EXAMPLE 15

Methyl (3-{4-[4-(6,7-dimethoxy-4-oxo-4H-chromen-3-yl)-butyl]-piperazin-1-yl}-phenyl)-carbamate

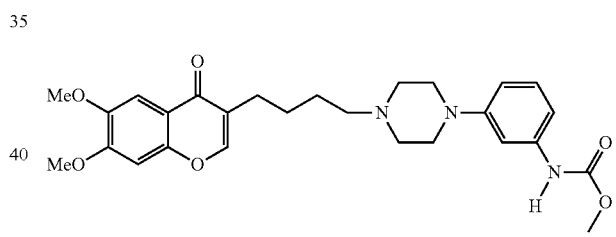

In a similar manner to Example 13, but using methyl chloroformate and 3-{4-[4-(3-aminophenyl)-piperazin-1-yl]-butyl}-6,7-dimethoxychromen-4-one obtained in Example 12, methyl (3-{4-[4-(6,7-dimethoxy-4-oxo-4H-chromen-3-yl)-butyl]-piperazin-1-yl}-phenyl)-carbamate is obtained.

EXAMPLE 16

7-{4-[4-(2,3-Dichlorophenyl)-piperazin-1-yl]-butyl}-[1,3]dioxolo[4,5-g]chromen-8-one

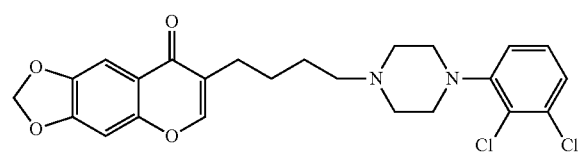 [SMILES: O=c1c(CCCCN2CCN(c3cccc(Cl)c3Cl)CC2)coc2cc3c(cc12)OCO3]

Step 1: Preparation of 6-bromo-1-(6-hydroxybenzo[1,3]dioxo-5-yl)-hexane-1-one

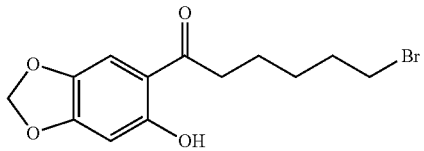 [SMILES: O=C(CCCCCBr)c1cc2c(cc1O)OCO2]

A solution of 1 g (7.2 mmol) of sesamol in 20 ml of CH$_2$Cl$_2$ is cooled to −10° C. with stirring. 1.1 ml (7.2 mmol) of 6-bromohexanoyl chloride is added, and then 1 g (7.6 mmol) of AlCl$_3$ in small portions. The temperature is allowed to rise to ambient temperature and stirring is maintained for 18 h. Hydrolysis is carried out by adding ice and acidification is carried out with concentrated HCl (2 ml). Extraction is carried out with CH$_2$Cl$_2$, and the organic phases, separated, dried over MgSO$_4$, filtered and evaporated, are subjected to flash chromatography over SiO$_2$ with a gradient of pure heptane to heptane-AcOEt 80-20 to obtain 500 mg of pale yellow crystals after evaporation (yield=22%) MS, ESI, m/z=314-316. $^1$H NMR (CDCl$_3$): 7.26 (s, 1H), 7.07 (s, 1H), 6.45 (s, 1H), 5.98 (s, 2H), 3.42 (t, 2H, J=6.8 Hz), 2.87 (t, 2H, J=7.6 Hz), 1.92 (m, 2H), 1.76 (m, 2H), 1.54 (m, 2H).

6-Bromo-1-(2-hydroxy-5-methoxyphenyl)-hexan-1-one is prepared in identical manner.

Step 2: Preparation of 6-[4-(2,3-dichlorophenyl)-piperazin-1-yl]-1-(6-hydroxybenzo[1,3]dioxol-5-yl)-hexan-1-one

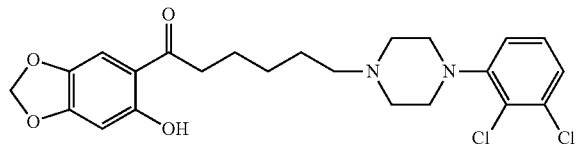 [SMILES: O=C(CCCCCN1CCN(c2cccc(Cl)c2Cl)CC1)c1cc2c(cc1O)OCO2]

950 mg (3 mmol) of the brominated derivative obtained in the above Step, 690 mg (3 mmol) of 2,3-dichlorophenylpiperazine, 1.3 ml (9 mmol) of triethylamine and 500 mg (3 mmol) of KI are added to 10 ml of CH$_3$CN. The mixture is refluxed, with stirring, for 20 h. Saturated NaHCO$_3$ solution (50 ml) is added, and extraction is carried out with AcOEt. The organic phases are separated, dried over MgSO$_4$, filtered and evaporated. Flash chromatography over SiO2 eluted with a gradient of pure CH$_2$Cl$_2$ to CH$_2$Cl$_2$-MeOH 90-10 allows, after evaporation and crystallisation in iPr$_2$O, 960 mg (yield=69%) of beige crystals to be obtained. $^1$H NMR (DMSO): 7.45 (s, 1H), 7.30 (m, 2H), 7.13 (m, 1H), 6.57 (s, 1H), 6.08 (s, 2H), 2.96 (m, 6H), 2.50 (m, 4H), 2.33 (m, 2H), 1.63 (m, 2H), 1.48 (m, 2H), 1.36 (m, 2H)

Step 3: 7-{4-[4-(2,3-Dichlorophenyl)-piperazin-1-yl]-butyl}-[1,3]dioxolo[4,5-g]chromen-8-one

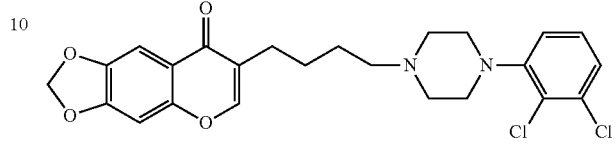

A solution of 600 mg (1.30 mmol) of the compound obtained in the above Step in 5 ml of dimethylformamide dimethylacetal is heated at 90° C. for 5 h with stirring. 50 ml of water are added and extraction with CH$_2$Cl$_2$ is carried out. The organic phases are separated, dried over MgSO$_4$, filtered and evaporated. Flash chromatography over SiO$_2$ eluted with a gradient of CH$_2$Cl$_2$ to CH$_2$Cl$_2$-MeOH 90-10 allows, after concentration and crystallisation in iPr2O, 250 mg (yield=40%) of beige crystals to be obtained. M.p. ° C.=140-142; analytical HPLC Xbridge C8, 4.6×250 mm, 5µ, eluant: CH$_3$CN—H$_2$O, KH$_2$PO$_4$ 40-60-6.8 g/l, pH4, r.t.=9.51 min; MS ESI, m/z=475-477; Anal C$_{24}$H$_{24}$N$_2$O$_4$Cl$_2$=475.38+0.21 H$_2$O, calc. C, % 60.64; H, % 5.09; N, % 5.89. found C, % 60.61; H, % 5.07; N, % 6.45. $^1$H NMR (DMSO): 8.17 (s, 1H), 7.33 (s, 1H), 7.29 (m, 2H), 7.22 (s, 1H), 7.13 (m, 1H), 6.02 (s, 2H), 2.96 (m, 4H), 2.50 (m, 6H), 2.35 (m, 2H), 1.51 (m, 4H).

EXAMPLE 17

7-{4-[4-(2,3-Difluorophenyl)-piperazin-1-yl]-butyl}-[1,3]dioxolo[4,5-g]chromen-8-one

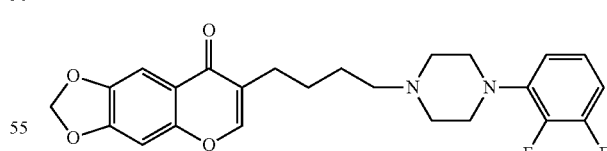

In an identical manner to the above Example 16, but using difluorophenylpiperazine, 7-{4-[4-(2,3-difluorophenyl)-piperazin-1-yl]-butyl}-[1,3]dioxolo[4,5-g]chromen-8-one is obtained. M.p. ° C.=140-142; analytical HPLC Xbridge C8, 4.6×250 mm, 5µ, eluant: CH$_3$CN—H$_2$O, KH$_2$PO$_4$ 35-65-6.8 g/l, pH4, r.t.=9.59 min; MS ESI, m/z=443 (MH+); Anal C$_{24}$H$_{24}$N$_2$O$_4$F$_2$=442.46+0.78 H$_2$O, calc. C, % 65.15; H, % 5.47; N, % 6.33. found C, % 65.41; H, % 5.71; N, % 6.77. $^1$H NMR (DMSO): 8.16 (s, 1H), 7.33 (s, 1H), 7.22 (s, 1H), 7.08

(m, 1H), 6.96 (m, 1H), 6.83 (t, 1H, J=8 Hz), 6.20 (s, 2H), 3.02 (m, 4H), 2.50 (m, 4H), 2.34 (m, 4H), 1.51 (m, 4H).

EXAMPLE 18

7-{4-[4-(3-Nitrophenyl)-piperazin-1-yl]-butyl}-[1,3] dioxolo[4,5-g]chromen-8-one

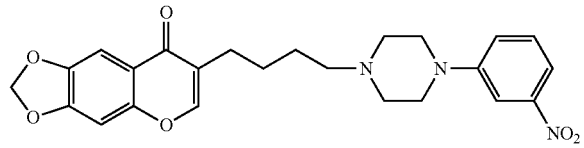

In an identical manner to the above Example 16, but using 3-nitrophenylpiperazine, 7-{4-[4-(3-nitrophenyl)-piperazin-1-yl]-butyl}-[1,3]dioxolo[4,5-g]chromen-8-one is obtained. MS ESI, m/z=452 (MH+); $^1$H NMR (DMSO): 8.17 (s, 1H), 7.62 (s, 1H), 7.57 (d, 1H, J=7.6 Hz), 7.46 (t, 1H, J=8.4 Hz), 7.39 (d, 1H, J=8.4 Hz), 7.33 (s, 1H), 7.22 (s, 1H), 6.20 (s, 2H), 3.24 (m, 4H), 2.50 (m, 4H), 2.35 (m, 4H), 1.50 (m, 4H).

EXAMPLE 19

7-{4-[4-(3-Aminophenyl)-piperazin-1-yl]-butyl}-[1, 3]dioxolo[4,5-g]chromen-8-one

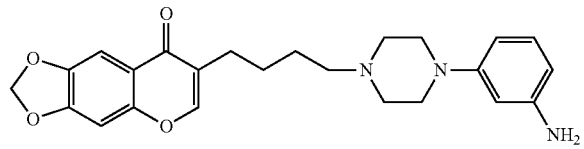 [SMILES: Nc1cccc(N2CCN(CCCCc3coc4cc5c(cc4c3=O)OCO5)CC2)c1]

In an identical manner to Example 12, but using the compound obtained in Example 18, the aniline 7-{4-[4-(3-aminophenyl)-piperazin-1-yl]-butyl}-[1,3]dioxolo-[4,5-g] chromen-8-one is obtained. MS ESI, m/z=422 (MH+); $^1$H NMR (CDCl3): 7.68 (s, 1H), 7.52 (s, 1H), 7.03 (t, 1H, J=8 Hz), 6.81 (s, 1H), 6.36 (d, 1H, J=8 Hz), 6.25 (d, 1H, J=2 Hz), 6.21 (d, 1H, J=7.6 Hz), 6.08 (s, 2H), 3.16 (m, 4H), 2.57 (m, 2H), 2.47 (t, 2H, J=6.4 Hz), 2.41 (t, 2H, J=7.6 Hz), 1.59 (m, 4H).

EXAMPLE 20

N-(3-{4-[4-(8-oxo-8H-[1,3]dioxolo[4,5-g]chromen-7-yl)-butyl]-piperazin-1-yl}-phenyl-acetamide

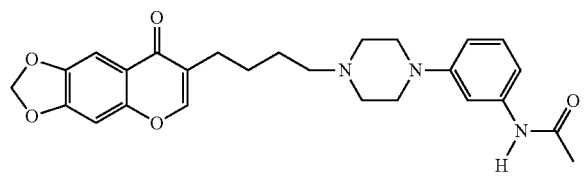 [SMILES: CC(=O)Nc1cccc(N2CCN(CCCCc3coc4cc5c(cc4c3=O)OCO5)CC2)c1]

In an identical manner to Example 14, but using 7-{4-[4-(3-aminophenyl)-piperazin-1-yl]-butyl}-[1,3]dioxolo[4,5-g] chromen-8-one instead of 3-{4-[4-(3-aminophenyl)-piperazin-1-yl]-butyl}-6,7-dimethoxychromen-4-one, N-(3-{4-[4-(8-oxo-8H-[1,3]dioxolo[4,5-g]chromen-7-yl)-butyl]-piperazin-1-yl}-phenyl)-acetamide is obtained.

EXAMPLE 21

N-(3-{4-[4-(8-oxo-8H-[1,3]dioxolo[4,5-g]chromen-7-yl)-butyl]-piperazin-1-yl}-phenyl)-methanesulfonamide

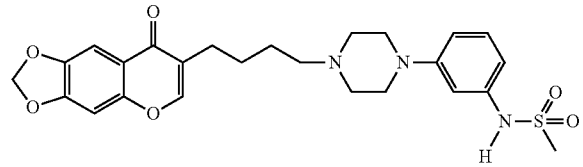 [SMILES: CS(=O)(=O)Nc1cccc(N2CCN(CCCCc3coc4cc5c(cc4c3=O)OCO5)CC2)c1]

In an analogous manner to Example 13, but using 7-{4-[4-(3-aminophenyl)-piperazin-1-yl]-butyl}-[1,3]dioxolo[4,5-g] chromen-8-one obtained in Example 19 instead of 3-{4-[4-(3-aminophenyl)-piperazin-1-yl]-butyl}-6,7-dimethoxychromen-4-one, N-(3-{4-[4-(8-oxo-8H-[1,3] dioxolo[4,5-g]chromen-7-yl)-butyl]-piperazin-1-yl}-phenyl)-methanesulfonamide is obtained. M.p. ° C.=174; analytical HPLC Xbridge C8, 4.6×250 mm, 5µ, eluant: CH$_3$CN—H$_2$O, KH$_2$PO$_4$ 25-75-6.8 g/l, pH4, r.t.=13.23 min; MS, ESI, m/z=499 (MH+); $^1$H NMR (DMSO): 9.51 (s, 1H), 8.16 (s, 1H), 7.33 (s, 1H), 7.22 (s, 1H), 7.13 (t, 1H, J=8.4 Hz), 6.73 (s, 1H), 6.67 (d, 1H, J=8.4 Hz), 6.63 (d, 1H), 6.20 (s, 2H), 3.07 (m, 4H), 2.94 (s, 3H), 2.47 (m, 4H), 2.36 (t, 2H, J=6.4 Hz and 6.8 Hz), 1.49 (m, 4H).

Hydrochloride: M.p. ° C.=260, Anal. C$_{25}$H$_{30}$ClN$_3$O$_6$S=499.59+0.34% H2O, calc. C, % 56.02; H, % 5.64; N, % 7.84; S, % 5.98. found C, % 56.37; H, % 5.69; N, % 7.65; S, % 6.89.

EXAMPLE 22

N-(3-{4-[4-(8-oxo-8H-[1,3]dioxolo[4,5-g]chromen-7-yl)-butyl]-piperazin-1-yl}-phenyl)-ethanesulfonamide

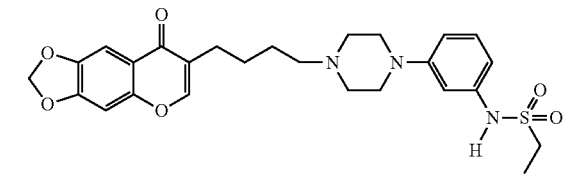 [SMILES: CCS(=O)(=O)Nc1cccc(N2CCN(CCCCc3coc4cc5c(cc4c3=O)OCO5)CC2)c1]

In an identical manner to Example 13, but using corresponding reactants, N-(3-{4-[4-(8-oxo-8H-[1,3]dioxolo[4,5-g]chromen-7-yl)-butyl]-piperazin-1-yl}-phenyl)-ethanesulfonamide is obtained. MS, ESI, m/z=514 (MH$^+$); $^1$H NMR of the hydrochloride (DMSO): 9.69 (s, 1H), 8.22 (s, 1H), 7.34 (s, 1H), 7.25 (s, 1H), 7.19 (t, 1H, J=8.4 Hz), 6.80 (s, 1H), 6.73 (m, 1H), 6.21 (s, 2H), 3.71 (m, 2H), 3.54 (m, 2H), 3.08 (m, 6H), 2.40 (m, 2H), 1.72 (m, 2H), 1.55 (m, 2H).

EXAMPLE 23

2-dimethylaminoethanesulfonic acid (3-{4-[4-(8-oxo-8H-[1,3]dioxolo[4,5-g]chromen-7-yl)-butyl]-piperazin-1-yl}-phenyl)-amide

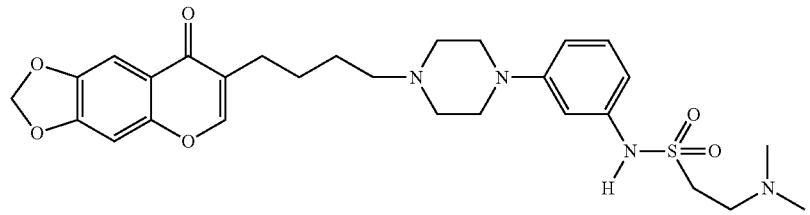 [SMILES: CN(C)CCS(=O)(=O)Nc1cccc(N2CCN(CCCCc3coc4cc5c(cc4c3=O)OCO5)CC2)c1]

Step 1: In a similar manner to Example 21, 7-{4-[4-(3-aminophenyl)-piperazin-1-yl]-butyl}-[1,3]dioxolo[4,5-g]chromen-8-one is condensed with 2-chloroethylsulfonyl chloride. (3-{4-[4-(8-oxo-8H-[1,3]dioxolo[4,5-g]chromen-7-yl)-butyl]-piperazin-1-yl}-phenyl)-ethenesulfonamide is obtained. $^1$H NMR (DMSO): 9.79 (s, 1H), 8.16 (s, 1H), 7.33 (s, 1H), 7.22 (s, 1H), 7.09 (t, 1H, J=8 Hz), 6.75 (dd, 1H, J=16.4 Hz and 10 Hz), 6.67 (d, 1H), 6.63 (dd, 1H, J=10 Hz and 2 Hz), 6.57 (dd, 1H, J=8 Hz and 1.2 Hz), 6.20 (s, 2H), 6.09 (d, 1H, J=16.4 Hz), 6.01 (d, 1H, J=9.6 Hz), 3.05 (m, 4H), 2.47 (m, 4H), 2.34 (m, 4H), 1.51 (m, 4H).

Step 2: The compound of the above Step 1 (100 mg, 0.2 mmol) is introduced into a sealed tube with 2 ml of 2M dimethylamine solution in MeOH at ambient temperature for 3 h. The batch is evaporated to dryness, and the residue is triturated with isopropanol HCl, the hydrochloride is introduced into iPr$_2$O and filtered. MS, ESI, m/z=557 (MH+); $^1$H NMR (DMSO) of the hydrochloride: 10.10 (s, 1H), 8.23 (s, 1H), 7.22 (m, 2H), 6.78 (m, 3H), 6.21 (s, 2H), 3.77 (m, 2H), 3.68 (m, 2H), 3.55 (m, 2H), 3.45 (m, 2H), 3.13 (m, 6H), 2.76 (s, 6H), 2.40 (m, 2H), 1.74 (m, 2H), 1.55 (m, 2H).

EXAMPLE 24

2-methoxyethanesulfonic acid (3-{4-[4-(8-oxo-8H-[1,3]dioxolo[4,5-g]chromen-7-yl)-butyl]-piperazin-1-yl}-phenyl)-amide

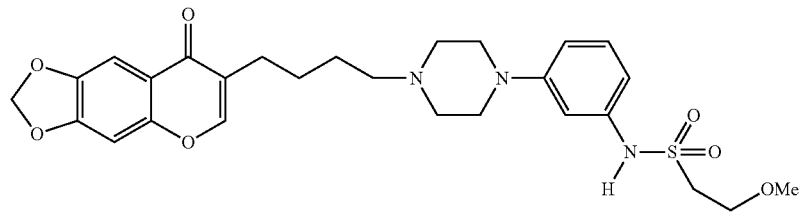 [SMILES: COCCS(=O)(=O)Nc1cccc(N2CCN(CCCCc3coc4cc5c(cc4c3=O)OCO5)CC2)c1]

In a similar manner to Example 23, a solution of sodium methoxide can be used with the intermediate of Step 1 of Example 23 to yield 2-methoxyethanesulfonic acid (3-{4-[4-(8-oxo-8H-[1,3]dioxolo[4,5-g]chromen-7-yl)-butyl]-piperazin-1-yl}-phenyl)-amide.

EXAMPLE 25

7-{4-[4-(1H-Indol-4-yl)-piperazin-1-yl]-butyl}-[1,3]dioxolo[4,5-g]chromen-8-one

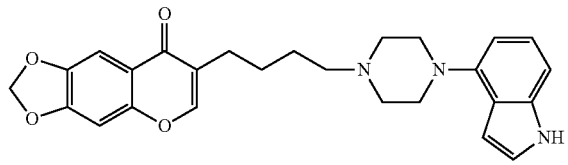 [SMILES: O=c1c(CCCCN2CCN(c3cccc4[nH]ccc34)CC2)coc2cc3c(cc12)OCO3]

By means of the same reaction sequence as indicated in Example 16, but using 4-indolylpiperazine, 7-{4-[4-(1H-indol-4-yl)-piperazin-1-yl]-butyl}-[1,3]dioxolo[4,5-g]chromen-8-one is obtained, M.p. ° C.=177-179; analytical HPLC Xbridge C8, 4.6×250 mm, 5μ, eluant: CH$_3$CN—H$_2$O, KH$_2$PO$_4$ 30-70-6.8 g/l, pH4, r.t.=9.69 min; MS, ESI, m/z=446 (MH$^+$); $^1$H NMR (DMSO): 11.0 (s, 1H), 9.51 (s, 1H), 8.18 (s, 1H), 7.33 (s, 1H), 7.23 (m, 2H), 7.00 (d, 1H, J=8 Hz), 6.94 (t, 1H, J=7.2 Hz), 6.42 (d, 1H, J=7.2 Hz), 6.34 (s, 1H), 6.20 (s, 2H), 3.09 (m, 4H), 2.57 (m, 4H), 2.37 (m, 4H), 1.51 (m, 4H).

Hydrochloride: Anal. C$_{26}$H$_{27}$N$_3$O$_4$, HCl=481.98+0.54% H$_2$O, calc. C, % 64.79; H, % 5.86; N, % 8.72. found C, % 63.78; H, % 5.70; N, % 8.46.

EXAMPLE 26

3-{4-[4-(3-Trifluoromethylphenyl)-piperazin-1-yl]-butyl}-6,7-dimethoxychromen-4-one

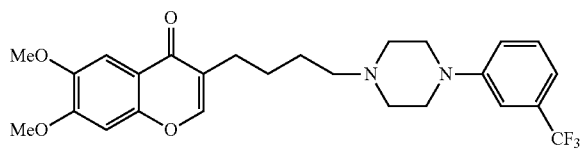 [SMILES: COc1cc2occ(CCCCN3CCN(c4cccc(C(F)(F)F)c4)CC3)c(=O)c2cc1OC]

By means of the same reaction sequence as in Steps 2 and 3 of Example 16, but using 6-bromo-1-(2-hydroxy-4,5-dimethoxyphenyl)-hexan-1-one prepared in Step 2 of Example 1, 3-{4-[4-(3-trifluoromethylphenyl)-piperazin-1-yl]-butyl}-6,7-dimethoxychromen-4-one is prepared in salt form with 1.5 equivalents of fumaric acid. M.p. ° C.=220; TLC: $SiO_2$ elution $CHCl_3$-MeOH 90-10, Rf=0.56; Anal. $C_{26}H_{29}F_3N_2O_4$, $C_6H_6O_6$=664.63, calc. C, % 57.82; H, % 5.30; N, % 4.21; F, % 8.57. found C, % 57.71; H, % 5.24; N, % 4.30; F, % 8.80%.

EXAMPLE 27

6-Methoxy-3-[4-(4-phenyl-piperazin-1-yl)-butyl]-chromen-4-one

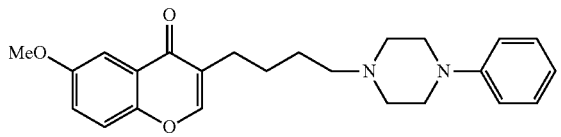 [SMILES: COc1ccc2occ(CCCCN3CCN(c4ccccc4)CC3)c(=O)c2c1]

By means of the same reaction sequence as in Steps 2 and 3 of Example 16, but using 6-bromo-1-(2-hydroxy-4-methoxyphenyl)-hexan-1-one prepared according to Steps 1 and of Example 1, and using 1,4-dimethoxybenzene instead of 1,2,4-trimethoxybenzene, or using 4-methoxyphenol as starting material in accordance with the same procedure as that in Step 1 of Example 16, 6-methoxy-3-[4-(4-phenyl-piperazin-1-yl)-butyl]-chromen-4-one is obtained, prepared in the form of white hydrochloride crystals. M.p. ° C.=198; TLC: $SiO_2$ elution $CHCl_3$-MeOH—$NH_4OH$ 95-4.5-0.5, Rf=0.45; Anal. $C_{24}H_{29}ClN_2O_3$=428.94, calc. C, % 67.20; H, % 6.81; N, % 6.53; Cl, % 8.26. found C, % 66.78; H, % 6.82; N, % 6.47; Cl, % 7.95%.

EXAMPLE 28

6-Methoxy-3-{4-[4-(2-methoxyphenyl)-piperazin-1-yl]-butyl}-chromen-4-one

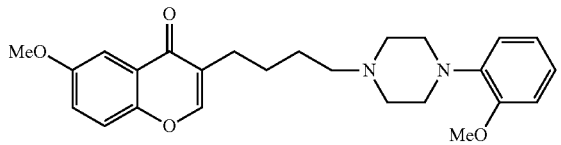 [SMILES: COc1ccc2occ(CCCCN3CCN(c4ccccc4OC)CC3)c(=O)c2c1]

In an identical manner to the above Example but using corresponding starting materials, 6-methoxy-3-{4-[4-(2-methoxyphenyl)-piperazin-1-yl]-butyl}-chromen-4-one is prepared in the form of white hydrochloride crystals. M.p. °C.=191; TLC: SiO2 elution $CHCl_3$-MeOH—$NH_4OH$ 95-4.5-0.5, Rf=0.67; Anal. $C_{25}H_{31}ClN_2O_4$=458.97, calc. C, % 65.42; H, % 6.81; N, % 6.10; Cl, % 7.72. found C, % 66.28; H, % 6.88; N, % 6.08; Cl, % 7.64%.

EXAMPLE 29

6-Methoxy-3-{4-[4-(3-trifluoromethylphenyl)-piperazin-1-yl]-butyl}-chromen-4-one

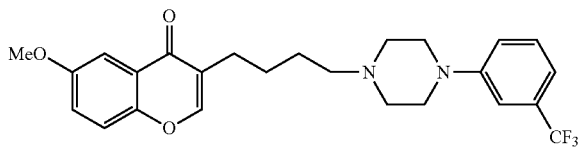

In an identical manner to the above Example but using corresponding starting materials, 6-methoxy-3-{4-[4-(3-trifluoromethylphenyl)-piperazin-1-yl]-butyl}-chromen-4-one is prepared in the form of white hydrochloride crystals. M.p. °C.=180; TLC: $SiO_2$ elution $CHCl_3$-MeOH—$NH_4OH$ 95-4.5-0.5, Rf=0.56; Anal. $C_{25}H_{28}ClF_3N_2O_3$=496.45, calc. C, % 60.42; H, % 5.68; N, % 5.64; Cl, % 7.13; F, % 11.48. found C, % 60.23; H, % 5.63; N, % 5.63; Cl, % 6.97%; F, % 11.28.

EXAMPLE 30

7-{4-[4-(2,3-Dichlorophenyl)piperazin-1-yl]-butyl}-6-methyl-[1,3]dioxolo[4,5-g]chromen-8-one

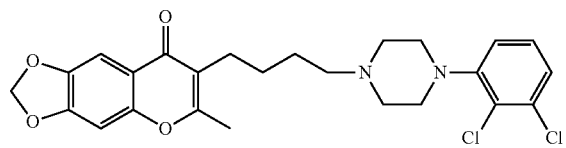 [SMILES: Cc1oc2cc3c(cc2c(=O)c1CCCCN1CCN(c2cccc(Cl)c2Cl)CC1)OCO3]

6-[4-(2,3-dichlorophenyl)-piperazin-1-yl]-1-(6-hydroxybenzo[1,3]dioxol-5-yl)-hexan-1-one (200 mg, 0.43 mmol) obtained in Step 2 of Example 16 is introduced into a microwave reaction vessel with 1 ml of dimethylacetamide dimethylacetal and heated at 160° C. for 5 min. The mixture is thrown into water and then extracted with AcOEt. The organic phases are separated, dried over $MgSO_4$, filtered and evaporated. Flash chromatography over $SiO_2$ with an elution gradient of $CH_2Cl_2$ to $CH_2Cl_2$-MeOH 90-10 allows, after evaporation and trituration in $iPr_2O$, 30 mg (yield 14%) of beige crystals to be obtained. M.p. ° C.=153-155; analytical HPLC Xbridge C8, 4.6×250 mm, 5μ., eluant: $CH_3CN$—$H_2O$, $KH_2PO_4$ 40-60-6.8 g/l, pH4, r.t.=11.09 min; MS, ESI, m/z=489-491 (MH+); ¹H NMR (DMSO): 7.29 (m, 3H), 7.16 (m, 2H), 6.18 (s, 2H), 2.96 (m, 4H), 2.45 (m, 6H), 2.40 (s, 3H), 2.35 (m, 2H), 1.46 (m, 4H).

EXAMPLE 31

6/7-Methoxy-7/6-hydroxy-3-{4-[4-(2-methoxyphenyl)-piperazin-1-yl]-butyl}-chromen-4-one

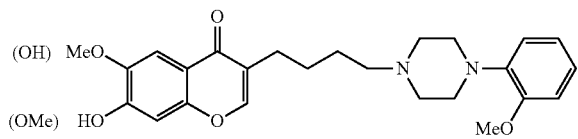 [SMILES: "(OMe)" ; "(OH)" ; COc1cc2c(=O)c(CCCCN3CCN(c4ccccc4OC)CC3)coc2cc1O]

This compound is obtained by the same reaction sequence as for Example 1 in Steps 3 and 4, but using as starting material 6-bromo-1-(2,4-dihydro-5-methoxyphenyl)hexan-1-one obtained as secondary product in Step 2 of the demethylation of Example 1. Analytical HPLC Xbridge C8, 4.6× 250 mm, 5µ, eluant: CH₃CN—H₂O, KH₂PO₄ 25-75-6.8 g/l, pH4, r.t.=11.27 min; MS, ESI, m/z=439 (MH⁺)

EXAMPLE 32

7-{4-[4-(6,7-Dimethoxy-4-oxo-4H-chromen-3-yl)-butyl]-piperazin-1-yl}-3H-benzoxazol-2-one

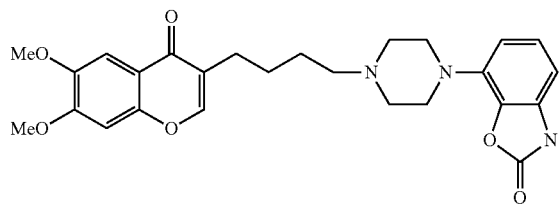 [SMILES: COc1cc2occ(CCCCN3CCN(c4cccc5[nH]c(=O)oc45)CC3)c(=O)c2cc1OC]

In a similar manner to Example 1, Step 4, but using 7-piperazin-1-yl-3H-benzoxazol-2-one described in *Bioorg. Med. Chem. Let.* 2001, 11, 2345, 7-{4-[4-(6,7-dimethoxy-4-oxo-4H-chromen-3-yl)-butyl]-piperazin-1-yl}-3H-benzoxazol-2-one is obtained.

EXAMPLE 33

4-{4-[4-(6,7-Dimethoxy-4-oxo-4H-chromen-3-yl)-butyl]-piperazin-1-yl}-1,3-dihydrobenzimidazol-2-one

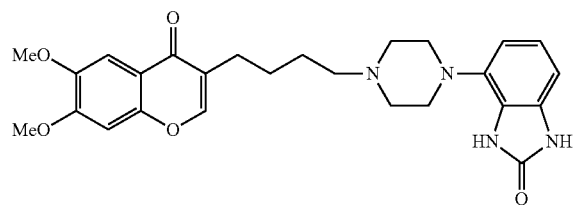 [SMILES: COc1cc2occ(CCCCN3CCN(c4cccc5[nH]c(=O)[nH]c45)CC3)c(=O)c2cc1OC]

In a similar manner to Example 1, Step 4, but using the hydrogenolysis derivative of 4-(4-benzylpiperazin-1-yl)-1,3-dihydrobenzimidazol-2-one described in *Bioorg. Med. Chem. Let.* 1998, 8, 2675, 4-{4-[4-(6,7-dimethoxy-4-oxo-4H-chromen-3-yl)-butyl]-piperazin-1-yl}-1,3-dihydrobenzimidazol-2-one is obtained.

The invention claimed is:
1. A compound of formula 1

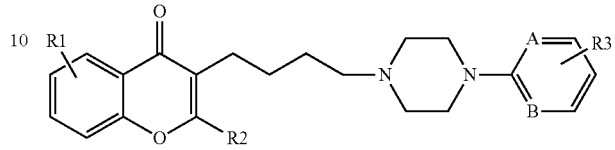

wherein:
R1 represents one or more identical or different substituent(s), each representing, independently, a hydrogen atom or a halogen atom, or a $C_{1-4}$alkoxy group or an OH group, or a $C_{1-4}$alkyl group or an —O(CH₂)ₙO— group in which n=1 or 2;
R2 represents a hydrogen atom or a $C_{1-4}$alkyl group;
A and B represent, independently, either a nitrogen atom or a carbon atom;
R3 represents a hydrogen atom or one or more identical or different substituent(s) selected from the group consisting of: a halogen atom, a $C_{1-4}$alkyl group, a $C_{1-4}$alkoxy or $C_{1-4}$thioalkoxy group, an —O(CH₂)ₙO— group in which n=1 or 2, an NO₂ group, an NHSO₂R4 group, an NHR5 group, an OH group, a $C_{1-4}$haloalkyl group, a CN group, a $C_{1-4}$alkoxycarbonyl group, a $C_{1-4}$alkylcarbonyl group, a $C_{1-4}$hydroxyalkyl group and a benzyl or phenyl substituent optionally substituted by a $C_{1-4}$alkoxy or a $C_{1-4}$alkyl group or a halogen atom,
or R3 constitutes a ring fused with the benzene ring carrying it, selected from the group consisting of a naphthalene, an indole, a benzimidazole, a carbostyril, a benzoxazolone and a benzimidazolone;
R4 represents a $C_{1-4}$alkyl group or a $C_{1-4}$dialkylamino group or a $C_{1-4}$alkoxyalkyl group or a $C_{1-4}$dialkylaminoalkyl group or a phenyl or phenyl-$C_{1-4}$alkyl group,
R5 represents a hydrogen atom or a $C_{1-4}$alkylcarbonyl group or a $C_{1-4}$alkoxy-carbonyl group,
or a pharmaceutically acceptable salt thereof.
2. A compound according to claim 1, wherein R1 represents one or more identical or different substituent(s) selected from the group consisting of a $C_{1-4}$alkoxy group, an OH group and an —O(CH₂)ₙO— group in which n=1 or 2.
3. A compound according to claim 1, wherein R2 represents a hydrogen atom.
4. A compound according to claim 1, wherein R3 represents a hydrogen atom when A and/or B represents a nitrogen atom.
5. A compound according to claim 1, wherein A and B simultaneously each represent a carbon atom.
6. A compound according to claim 1, wherein R3 represents one or more identical or different substituent(s) selected from the group consisting of: a halogen atom, a $C_{1-4}$alkoxy group, an —O(CH₂)ₙO— group in which n=1 or 2, an NHSO₂R4 group, an OH group and a CN group.
7. A compound according to claim 1, wherein R3, together with the benzene ring carrying it, represents an indole group or a benzimidazole group or a carbostyril group.
8. A compound according to claim 1, wherein the compound is selected from the group consisting of:
6,7-dimethoxy-3-{4-[4-(2-methoxyphenyl)-piperazin-1-yl]-butyl}-chromen-4-one;

3-{4-[4-(6,7-dimethoxy-4-oxo-4H-chromen-3-yl)-butyl]-piperazin-1-yl}-benzonitrile;
3-{4-[4-(2,3-dichlorophenyl)-piperazin-1-yl]-butyl}-6,7-dimethoxychromen-4-one;
3-{4-[4-(3-hydroxyphenyl)-piperazin-1-yl]-butyl}-6,7-dimethoxychromen-4-one;
6,7-dimethoxy-3-[4-(4-pyrimidin-2-yl-piperazin-1-yl)-butyl]-chromen-4-one;
6,7-dimethoxy-3-[4-(4-pyridin-2-yl-piperazin-1-yl)-butyl]-chromen-4-one;
3-{4-[4-(2,3-difluorophenyl)-piperazin-1-yl]-butyl}-6,7-dimethoxychromen-4-one;
3-{4-[4-(1H-benzimidazol-4-yl-)piperazin-1-yl]-butyl}-6,7-dimethoxychromen-4-one;
3-{4-[4-(1H-indol-4-yl)-piperazin-1-yl]-butyl}-6,7-dimethoxychromen-4-one;
5-{4-[4-(6,7-dimethoxy-4-oxo-4H-chromen-3-yl)-butyl]-piperazin-1-yl}-1H-quinolin-2-one;
6,7-dimethoxy-3-{4-[4-(3-nitrophenyl)-piperazin-1-yl]-butyl}-chromen-4-one;
3-{4-[4-(3-aminophenyl)-piperazin-1-yl]-butyl}-6,7-dimethoxychromen-4-one;
N-(3-{4-[4-(6,7-dimethoxy-4-oxo-4H-chromen-3-yl)-butyl]-piperazin-1-yl}-phenyl)-methanesulfonamide;
N-(3-{4-[4-(6,7-dimethoxy-4-oxo-4H-chromen-3-yl)-butyl]-piperazin-1-yl}-phenyl)-acetamide;
methyl (3-{4-[4-(6,7-dimethoxy-4-oxo-4H-chromen-3-yl)-butyl]-piperazin-1-yl}-phenyl)-carbamate;
7-{4-[4-(2,3-dichlorophenyl)-piperazin-1-yl]-butyl}-[1,3]dioxolo[4,5-g]chromen-8-one;
7-{4-[4-(2,3-difluorophenyl)-piperazin-1-yl]-butyl}-[1,3]dioxolo[4,5-g]chromen-8-one;
7-{4-[4-(3-nitrophenyl)-piperazin-1-yl]-butyl}-[1,3]dioxolo[4,5-g]chromen-8-one;
7-{4-[4-(3-aminophenyl)-piperazin-1-yl]-butyl}-[1,3]dioxolo[4,5-g]chromen-8-one;
N-(3-{4-[4-(8-oxo-8H-[1,3]dioxolo[4,5-g]chromen-7-yl)-butyl]-piperazin-1-yl}-phenyl-acetamide;
N-(3-{4-[4-(8-oxo-8H-[1,3]dioxolo[4,5-g]chromen-7-yl)-butyl]-piperazin-1-yl}-phenyl)-methanesulfonamide;
N-(3-{4-[4-(8-oxo-8H-[1,3]dioxolo[4,5-g]chromen-7-yl)-butyl]-piperazin-1-yl}-phenyl)-ethanesulfonamide;
2-dimethylaminoethanesulfonic acid (3-{4-[4-(8-oxo-8H-[1,3]dioxolo[4,5-g]chromen-7-yl)-butyl]-piperazin-1-yl}-phenyl)-amide;
2-methoxyethanesulfonic acid (3-{4-[4-(8-oxo-8H-[1,3]dioxolo[4,5-g]chromen-7-yl) -butyl]-piperazin-1-yl}-phenyl)-amide;
7-{4-[4-(1H-indol-4-yl)-piperazin-1-yl]-butyl}-[1,3]dioxolo[4,5-g]chromen-8-one;
3-{4-[4-(3-trifluoromethylphenyl)-piperazin-1-yl]-butyl}-6,7-dimethoxychromen-4-one;
6-methoxy-3-[4-(4-phenyl-piperazin-1-yl)-butyl]-chromen-4-one;
6-methoxy-3-{4-[4-(2-methoxyphenyl)-piperazin-1-yl]-butyl}-chromen-4-one;
6-methoxy-3-{4-[4-(3-trifluoromethylphenyl)-piperazin-1-yl]-butyl}-chromen-4-one;
7-{4-[4-(2,3-dichlorophenyl)piperazin-1-yl]-butyl}-6-methyl-[1,3]dioxolo[4,5-g]chromen-8-one;
6,7-methoxy-7,6-hydroxy-3-{4-[4-(2-methoxyphenyl)-piperazin-1-yl]-butyl}-chromen-4-one;
7-{4-[4-(6,7-dimethoxy-4-oxo-4H-chromen-3-yl}-piperazin-1-yl}-3H-benzoxazol-2-one; and
4-{4-[4-(6,7-dimethoxy-4-oxo-4H-chromen-3-yl)-butyl]-piperazin-1-yl}-1,3-dihydrobenzimidazol-2-one.

9. A method for the preparation of a compound of formula 1 according to claim 1, wherein chromone of formula 4, which can be substituted or non substituted, is prepared, and said chromone of formula 4 is reacted with a piperazine of formula 5:

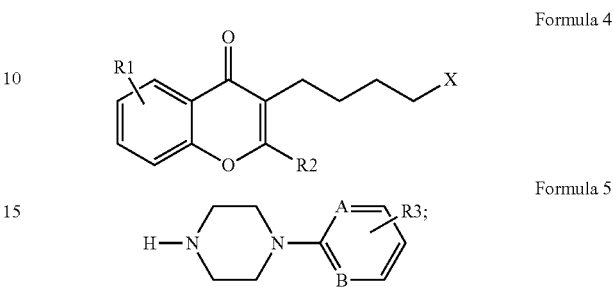

Formula 4

Formula 5 and X represents Cl, Br, or I.

10. A method for the preparation of a compound of formula 1 according to claim 1, wherein a phenol derivative of formula 6, which can be substituted or unsubstituted, is prepared starting from a compound of formula 3,

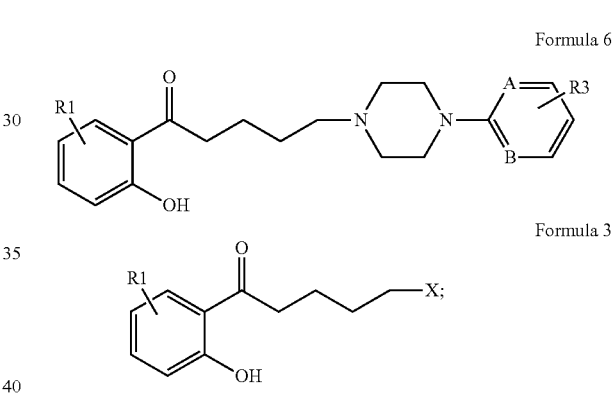

Formula 6

Formula 3 under alkylation conditions in the presence of a base, in a solvent, and X represents Cl or Br, and the compound of formula 6 is then reacted with DMF or the dimethylacetal of DMF or of DMA.

11. A pharmaceutical composition comprising at least one compound according to claim 1, or a pharmaceutically acceptable salt thereof, and a pharmaceutically acceptable excipient.

12. A method for the treatment of a neurological or psychiatric disease or disorder or erectile dysfunction or dependency on drugs and on addictive substances wherein said method comprises administering a compound according to claim 1 which inhibits the D3 receptor according to claim 1 to a subject in need thereof.

13. A method according to claim 12, wherein the neurological or psychiatric disease or disorder or erectile dysfunction or dependence on drugs and on addictive substances is selected from the group consisting of: Parkinson's disease, psychosis, schizophrenia, dyskinesias associated with Parkinson's disease, cognitive deficiency optionally associated with age or with Alzheimer's disease, mood disorder, essential tremor, anxiety, depression, bipolar disorder, sexual impotence, premature ejaculation, alcoholism and nicotine addiction.

14. The method according to claim 10, wherein the base is selected from $K_2CO_3$, $Cs_2CO_3$, or $NEt_3$.

15. The method of according to claim 14, wherein the solvent is selected from acetonitrile, or methyl ethyl ketone.

* * * * *